(12) United States Patent
Vo

(10) Patent No.: US 8,870,968 B2
(45) Date of Patent: Oct. 28, 2014

(54) PROSTHETIC DEVICES AND METHODS OF MAKING AND USING THE SAME

(75) Inventor: Ha Van Vo, Macoa, GA (US)

(73) Assignee: The Corporation of Mercer University, Macon, GA (US)

( * ) Notice: Subject to any disclaimer, the term of this patent is extended or adjusted under 35 U.S.C. 154(b) by 135 days.

(21) Appl. No.: 13/476,741

(22) Filed: May 21, 2012

(65) Prior Publication Data
US 2012/0303135 A1    Nov. 29, 2012

Related U.S. Application Data

(60) Provisional application No. 61/490,124, filed on May 26, 2011.

(51) Int. Cl.
| | | |
|---|---|---|
| *A61F 2/66* | (2006.01) | |
| *A61F 2/80* | (2006.01) | |
| *A61F 2/60* | (2006.01) | |
| *A61F 2/64* | (2006.01) | |
| *A61F 2/50* | (2006.01) | |
| *A61F 2/68* | (2006.01) | |
| *A61F 2/78* | (2006.01) | |

(52) U.S. Cl.
CPC ........... *A61F 2/80* (2013.01); *A61F 2002/6657* (2013.01); *A61F 2/60* (2013.01); *A61F 2/64* (2013.01); *A61F 2/66* (2013.01); *A61F 2002/5003* (2013.01); *A61F 2002/5009* (2013.01); *A61F 2002/502* (2013.01); *A61F 2002/5043* (2013.01); *A61F 2002/5072* (2013.01); *A61F 2002/608* (2013.01); *A61F 2002/6621* (2013.01); *A61F 2002/6635* (2013.01); *A61F 2002/665* (2013.01); *A61F 2002/6671* (2013.01); *A61F 2002/6692* (2013.01); *A61F 2002/6854* (2013.01); *A61F 2002/7862* (2013.01); *A61F 2002/7881* (2013.01)
USPC .................... 623/33; 623/38; 623/55; 623/32

(58) Field of Classification Search
CPC ................ A61F 2002/6657; A61F 2002/6671; A61F 2002/7862; A61F 2002/6664; A61F 2002/6685; A61F 2002/6692
See application file for complete search history.

(56) References Cited

U.S. PATENT DOCUMENTS

| | | | | |
|---|---|---|---|---|
| 61,780 | A | * | 2/1867 | Watson ........................... 623/33 |
| 1,211,222 | A | * | 1/1917 | Pilling et al. .................... 623/33 |

(Continued)

FOREIGN PATENT DOCUMENTS

| | | | | |
|---|---|---|---|---|
| DE | 2540138 | | 3/1997 | |
| DE | 101 07 838 A1 | * | 9/2002 | ................ A61F 2/66 |

(Continued)

OTHER PUBLICATIONS

PCT/US2010/026435 International Search Report and Written Opinion, May 7, 2010.

Primary Examiner — David H Willse
(74) Attorney, Agent, or Firm — Withers & Keys, LLC

(57) ABSTRACT

Prosthetic devices containing an artificial foot are disclosed. Methods of making and using prosthetic devices containing an artificial foot are also disclosed. The artificial foot may be in the form of a thermoformed foot member having at least one foot member curved section between a foot member first end and a foot member second end opposite the foot member first end such that (a) a first portion of a foot member inner surface overlaps and faces a second portion of the foot member inner surface, (b) a foot member second end surface is positioned (i) between and connecting a foot member outer surface and the foot member inner surface to one another and (ii) over and facing the foot member second end surface along the at least one foot member curved section.

17 Claims, 15 Drawing Sheets

(56) References Cited

U.S. PATENT DOCUMENTS

| | | | |
|---|---|---|---|
| 4,634,446 A * | 1/1987 | Kristinsson | 623/33 |
| 5,112,356 A * | 5/1992 | Harris et al. | 623/49 |
| 5,116,383 A | 5/1992 | Shorter et al. | |
| 5,507,838 A | 4/1996 | Chen | |
| 5,944,760 A | 8/1999 | Christensen | |
| 6,197,066 B1 | 3/2001 | Gabourie | |
| 7,178,218 B1 * | 2/2007 | Houser et al. | 29/558 |
| 2004/0137178 A1 | 7/2004 | Janusson et al. | |
| 2007/0225824 A1 | 9/2007 | Einarsson | |
| 2008/0228288 A1 * | 9/2008 | Nelson et al. | 623/55 |

FOREIGN PATENT DOCUMENTS

| | | |
|---|---|---|
| GB | 253729 | 6/1926 |
| WO | 2009/012774 | 1/2009 |
| WO | 2009/015896 | 2/2009 |

\* cited by examiner

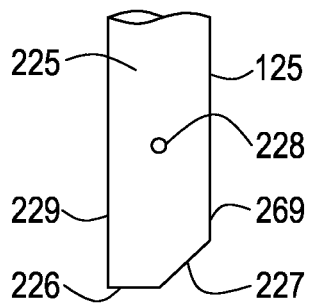
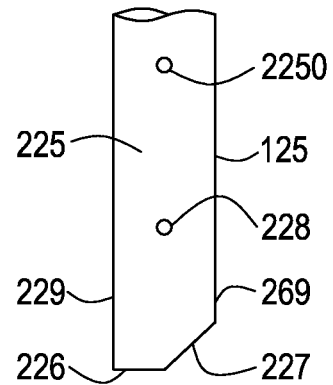
FIG. 11A                FIG. 11B
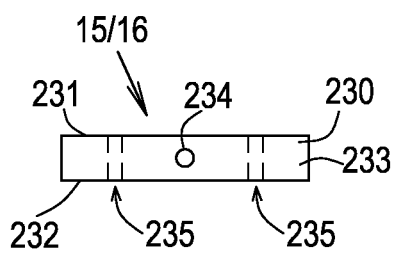
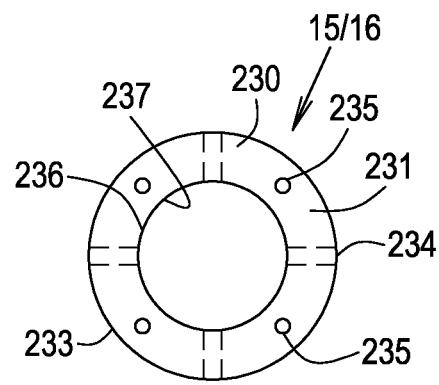
FIG. 12A                FIG. 12B
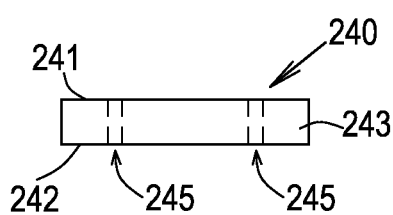
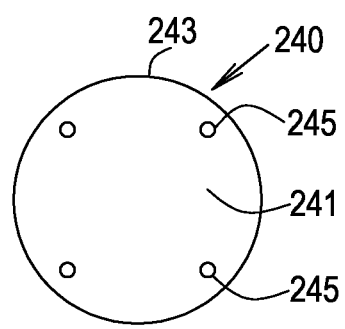
FIG. 13A                FIG. 13B
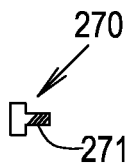
FIG. 14

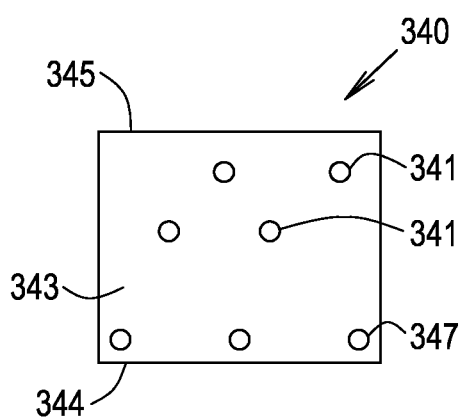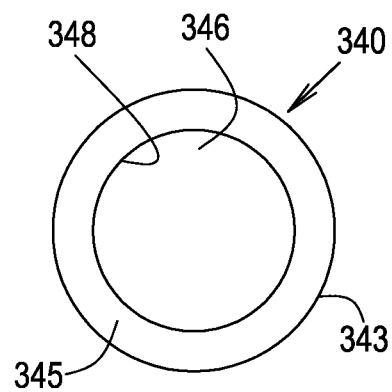
FIG. 15A  FIG. 15B
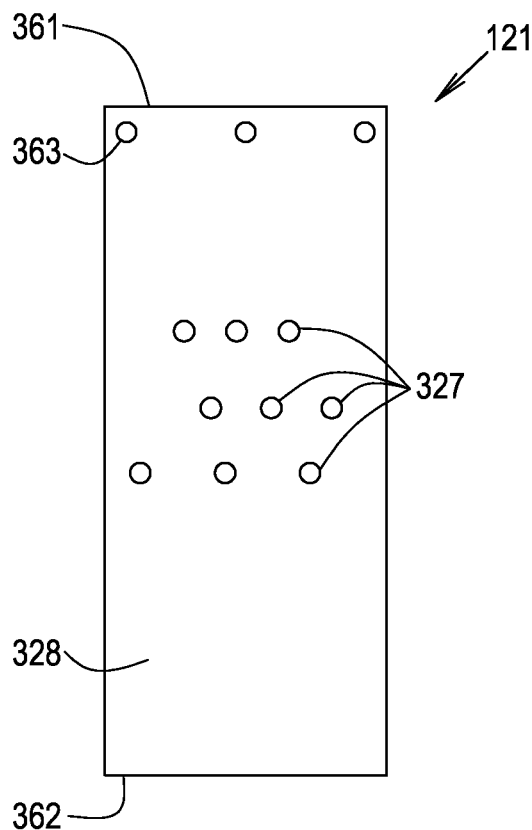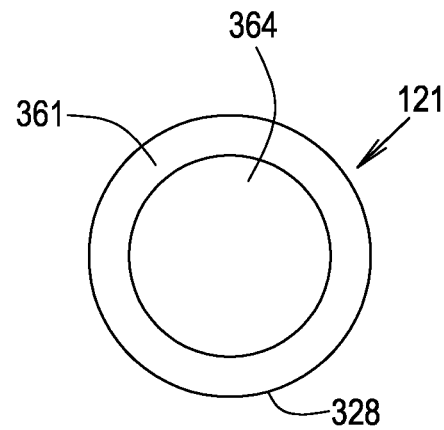
FIG. 16A  FIG. 16B

PROSTHETIC DEVICES AND METHODS OF MAKING AND USING THE SAME

This application claims the benefit of priority to U.S. Provisional Patent Application Ser. No. 61/490,124 filed on 26 May 2011, and entitled "PROSTHETIC DEVICES AND METHODS OF MAKING AND USING THE SAME," the subject matter of which is incorporated by reference herein in its entirety.

TECHNICAL FIELD

The present invention relates to prosthetic devices. The present invention also relates to methods of making and methods of using prosthetic devices.

BACKGROUND

A customized socket for an amputee costs from about $3,500 to $7,000. In addition, the distal attachments of the socket include a pylon, ankle, and foot for below knee amputation; these components cost about $500 to $3,000. For an above-knee amputation, the distal attachments of the socket include the knee, pylon, ankle, and foot; these components cost about $1,200 to $6,000. Total cost for a below-knee amputation prosthesis is from about $4,000 to $10,000 and about $4,700 to $13,000 for an above-knee amputation prosthesis in the USA (source—Hanger Prosthetics & Orthotics Inc. (Macon, Ga.)).

In third world countries, especially post-war countries such as Vietnam, Korea, Afghanistan, Cambodia, Laos, Iraq, and Haiti, amputees cannot afford the above-mentioned prices for prosthesis. What is needed in the art is a relatively inexpensive, effective prosthesis.

Efforts continue to further develop relatively inexpensive, effective prosthesis for use anywhere, and especially in third world countries.

SUMMARY

The present invention addresses some of the difficulties and problems discussed above by further development and discovery of inexpensive prosthesis devices comprising (i) an artificial foot component, and optionally (iii) an artificial knee component. In some exemplary embodiments, the disclosed prosthesis devices comprise (1) an artificial foot component, optionally in combination with (2) an artificial knee component and/or (3) the universal prosthetic socket (a) disclosed in the present invention or (b) previously disclosed in (i) International Patent Application No. PCT/US2010/026435, (ii) U.S. Provisional Patent Application Ser. No. 61/157,767 and (iii) U.S. Provisional Patent Application Ser. No. 61/183,095, the subject matter of all of which is incorporated by reference herein in its entirety, in combination with one or more additional prosthesis components such as an artificial foot and an artificial knee. The artificial foot may further comprise one or more additional features including, but not limited to, a cushioning member, a sole member, and an upper foot member.

Accordingly, in one exemplary embodiment, the present invention is directed to prosthetic devices comprising an artificial foot. In some exemplary embodiments, the disclosed prosthetic devices comprise an artificial foot comprising a thermoformed foot member having a foot member first end, a foot member second end opposite the foot member first end, at least one foot member curved section between the foot member first end and the foot member second end, a foot member outer surface extending between the foot member first end to the foot member second end, a foot member inner surface extending between the foot member first end to the foot member second end, and a foot member thickness extending between the foot member outer surface and the foot member inner surface, wherein (a) a first portion of said foot member inner surface overlaps and faces a second portion of said foot member inner surface, (b) a foot member second end surface is positioned (i) between and connecting said foot member outer surface and said foot member inner surface to one another and (ii) over and facing said foot member inner surface, and (c) said foot member thickness is substantially constant from said foot member second end surface along said at least one foot member curved section.

In some embodiments, the disclosed prosthetic devices may comprise an artificial foot comprising a thermoformed foot member having a foot member first end, a foot member second end opposite the foot member first end, at least one foot member curved section between the foot member first end and the foot member second end, a foot member outer surface extending between the foot member first end to the foot member second end, a foot member inner surface extending between the foot member first end to the foot member second end, and a foot member thickness extending between the foot member outer surface and the foot member inner surface, wherein the foot member further comprises a groove therein, wherein the groove (i) comprises opposing groove side surfaces, (ii) extends across a width of the foot member proximate a toe portion of the foot member, and (iii) extends a depth into the foot member from the foot member inner surface toward the foot member outer surface. The groove may also extend through other artificial foot components such as the cushioning member and the upper foot member, when present. Further, the groove may have any desired shape, for example, a V-shaped groove or a U-shaped groove or a υ-shaped groove.

In another exemplary embodiment, the present invention is directed to prosthetic devices comprising an artificial knee. In some exemplary embodiments, the disclosed prosthetic devices comprise an artificial knee comprising an artificial knee member having (i) an upper end configured to be attachable to an above-knee portion of a rigid member; (ii) a lower end configured to be attachable to a below-knee portion of the rigid member; (iii) a channel extending along the upper end and through the artificial knee member from proximate a front portion to a rear portion of the artificial knee member, the channel having a channel surface forming opposite channel side surfaces and a channel floor surface positioned between the opposite channel side surfaces; (iv) a horizontally extending connecting hole extending through an upper portion of the artificial knee member, the horizontally extending connecting hole extending from a first portion of an outer peripheral surface of the artificial knee member, out of one channel side surface, through the channel, into an opposite channel side surface, and out of a second portion of the outer peripheral surface of the artificial knee member opposite the first portion of the outer peripheral surface of the artificial knee member; (v) a centrally located hollow portion extending into a lower surface of the lower end, the centrally located hollow portion having a hollow portion cross-sectional area corresponding to an outer cross-sectional area of a connecting portion of the below-knee portion of the rigid member; and (vi) a set of horizontally extending holes extending from the outer peripheral surface of the artificial knee member to the centrally located hollow portion, each hole of which is sized to accommodate a fastener within a set of fasteners. The artificial knee member may further comprise one or more additional features including, but not limited to, a tensioning member channel or groove extending through the artificial knee member from the channel floor surface to a cut-out section along the front portion of the lower end; a tensioning member channel or groove extending along an outer surface of the artificial knee member from the upper end to a cut-out section along the front portion of the lower end; and/or a tensioning member positioned within the tensioning member channel or along the groove surface and connecting the front portion of the lower end to the above-knee portion of the rigid member.

In yet another exemplary embodiment, the present invention is directed to prosthetic devices comprising (i) the artificial foot as described herein in combination with at least one of (ii) the artificial knee as described herein, and (iii) a socket operatively adapted and sized to receive a user's stump. In some exemplary embodiments, the disclosed prosthetic devices comprise (i) the artificial foot as described herein in combination with at least one of (ii) the artificial knee as described herein, and (iii) a universal socket operatively adapted and sized to receive a variety of stump sizes, wherein the universal socket comprises a first socket open end sized to receive a user stump, a second socket end opposite the first socket end, and at least two differently sized socket regions positioned between the first socket open end and the second socket end, the at least two differently sized socket regions comprising an upper socket region proximate the first socket open end and a lower socket region positioned between the upper socket region and the second socket end, wherein the upper socket region has an upper region cross-sectional area, the lower socket region has an lower region cross-sectional area, and the upper region cross-sectional area is greater than the lower region cross-sectional area; and a rigid member extending from and connecting the second socket end to the artificial foot, the artificial knee or both.

In yet another exemplary embodiment, the present invention is directed to prosthetic devices comprising a universal socket, alone or in combination with an artificial foot and/or an artificial knee as described herein, wherein the universal socket is operatively adapted and sized to receive a variety of stump sizes, the universal socket comprising a first socket open end sized to receive a user stump; a second socket end opposite the first socket end; at least two differently sized socket regions positioned between the first socket open end and the second socket end, the at least two differently sized socket regions comprising an upper socket region proximate the first socket open end and a lower socket region positioned between the upper socket region and the second socket end, wherein the upper socket region has an upper region cross-sectional area, the lower socket region has an lower region cross-sectional area, and the upper region cross-sectional area is greater than the lower region cross-sectional area; and at least one slot extending from the first socket open end towards the second socket end, wherein each slot has (i) a horizontal slot component within the upper socket region, and (ii) a vertical slot component extending from the horizontal slot component towards the lower socket region.

The present invention is further directed to a method of making prosthetic devices comprising (i) the artificial foot as described herein, (ii) the artificial knee as described herein, (iii) the universal socket as described herein, or (iv) any combination of the artificial foot, the artificial knee and the universal socket as described herein. The disclosed method of making a prosthetic device may comprise one or more of the following steps selected from: forming a thermoformed artificial foot; forming a cushioning member; forming a sole member; forming an upper foot member; forming a universal socket; forming one or more straps for attaching a universal socket to a user's stump (i.e., leg portion); forming a rigid member, wherein the rigid member comprises (i) a single rigid member, (ii) a combination of an upper rigid member and a lower rigid member, (iii) a combination of an above-knee portion of a rigid member and a below-knee portion of a rigid member, (iv) a combination of an above-knee portion of a rigid member and a below-knee portion of the rigid member, wherein the below-knee portion comprises the upper rigid member and the lower rigid member, or (v) a combination of an above-knee portion of a rigid member and a below-knee portion of the rigid member, wherein the above-knee portion comprises a first upper rigid member and a first lower rigid member and the below-knee portion comprises a second upper rigid member and a second lower rigid member so that a length of each of the above-knee and below-knee portions is independently adjustable; forming a socket connector plate; forming a socket connector member; forming a foot connector member; forming a tubular connector; forming an artificial knee member; forming a tensioning member; and attaching one or more of the above-mentioned components to one another via adhesive (e.g., attaching the thermoformed foot member to the cushioning member and the sole member); fasteners (such as screws, nuts and bolts, etc.) (e.g., attaching the universal socket to the rigid member, the socket connector plate to the socket connector member, foot connector member to the thermoformed foot member and the tubular connector, and the rigid member to the artificial knee member); or clamps (e.g., attaching the tensioning member to the artificial knee member, the above-knee portion of the rigid member, or to itself).

The present invention is even further directed to a method of using any of the herein disclosed prosthetic devices.

These and other features and advantages of the present invention will become apparent after a review of the following detailed description of the disclosed embodiments and the appended claims.

BRIEF DESCRIPTION OF THE FIGURES

FIG. 11A depicts a side view of an exemplary above-knee member shown in FIG. 5A or FIG. 5B as viewed along direction line F;

FIG. 11B depicts a side view of an exemplary above-knee member shown in FIG. 5C as viewed along direction line F;

FIG. 12A depicts a side view of an exemplary foot or socket connector member suitable for use in the exemplary prosthetic devices shown in FIGS. 1A, 1B, 4A and 4B;

FIG. 12B depicts a top view of the exemplary foot or socket connector member shown in FIG. 12A;

FIG. 13A depicts a side view of an exemplary socket connector plate suitable for use in the exemplary prosthetic devices shown in FIGS. 1A, 1B, 4A and 4B;

FIG. 13B depicts a top view of the exemplary socket connector plate shown in FIG. 13A;

FIG. 14 depicts a side view of an exemplary fastener in the form of a screw;

FIG. 15A depicts a side view of an exemplary tubular connector suitable for use in the exemplary prosthetic devices shown in FIGS. 1A, 1B, 4A and 4B;

FIG. 15B depicts a top view of the exemplary tubular connector shown in FIG. 15A;

FIG. 16A depicts a side view of an exemplary upper rigid member suitable for use in the exemplary prosthetic devices shown in FIGS. 1A, 1B, 4A and 4B;

FIG. 16B depicts a top view of the exemplary upper rigid member shown in FIG. 16A;

DETAILED DESCRIPTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

The present invention is directed to prosthetic devices comprising (i) an artificial foot as described herein; (ii) an artificial knee as described herein; (iii) a universal socket as described herein; or (iv) any combination of the artificial foot, the artificial knee, and/or the universal socket as described herein, either alone or in combination with a socket operatively adapted and sized to receive a user's stump, for example, a universal socket as disclosed in International Patent Application No. PCT/US2010/026435 (as well as any and all of the components disclosed for use along with the universal socket as disclosed in International Patent Application No. PCT/US2010/026435), the subject matter of which is incorporated herein by reference in its entirety.

The present invention is further directed to methods of making prosthetic devices comprising (i) an artificial foot as described herein; (ii) an artificial knee as described herein; (iii) a universal socket as described herein; or (iv) any combination of the artificial foot, the artificial knee, and/or the universal socket as described herein, either alone or in combination with, any other socket operatively adapted and sized to receive a user's stump. The present invention is even further directed to methods of using prosthetic devices comprising (i) an artificial foot as described herein; (ii) an artificial knee as described herein; (iii) a universal socket as described herein; or (iv) any combination of the artificial foot, the artificial knee, and/or the universal socket as described herein, either alone or in combination with, any other socket operatively adapted and sized to receive a user's stump, for example, a universal socket as disclosed in International Patent Application No. PCT/US2010/026435 (as well as any and all of the components disclosed for use along with the universal socket as disclosed in International Patent Application No. PCT/US2010/026435).

Figure 1A:
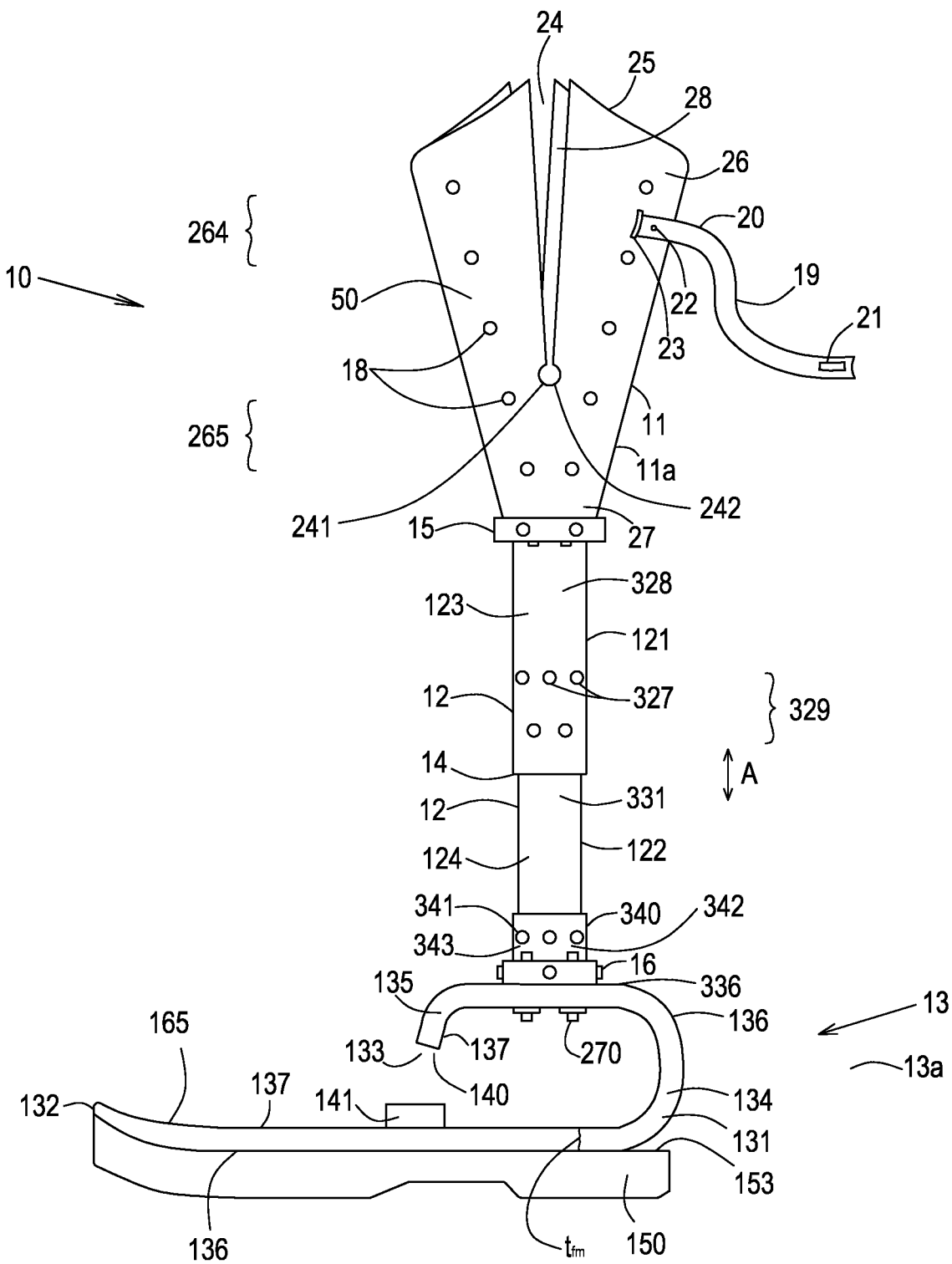
FIGS. 1A-1B depict views of exemplary prosthetic devices of the present invention.

An exemplary prosthetic device of the present invention is shown in FIG. 1A. As shown in FIG. 1A, exemplary prosthetic device 10 comprises a universal socket 11 (also referred to herein as universal socket 11a) operatively adapted and sized to receive a variety of stump sizes (not shown); an artificial foot 13 (also referred to herein as artificial foot 13a); a rigid member 12 extending from and connecting a second socket end 27 of universal socket 11a to artificial foot member 13a; a socket connector member 15; and a foot connector member 16.

Figure 1B:
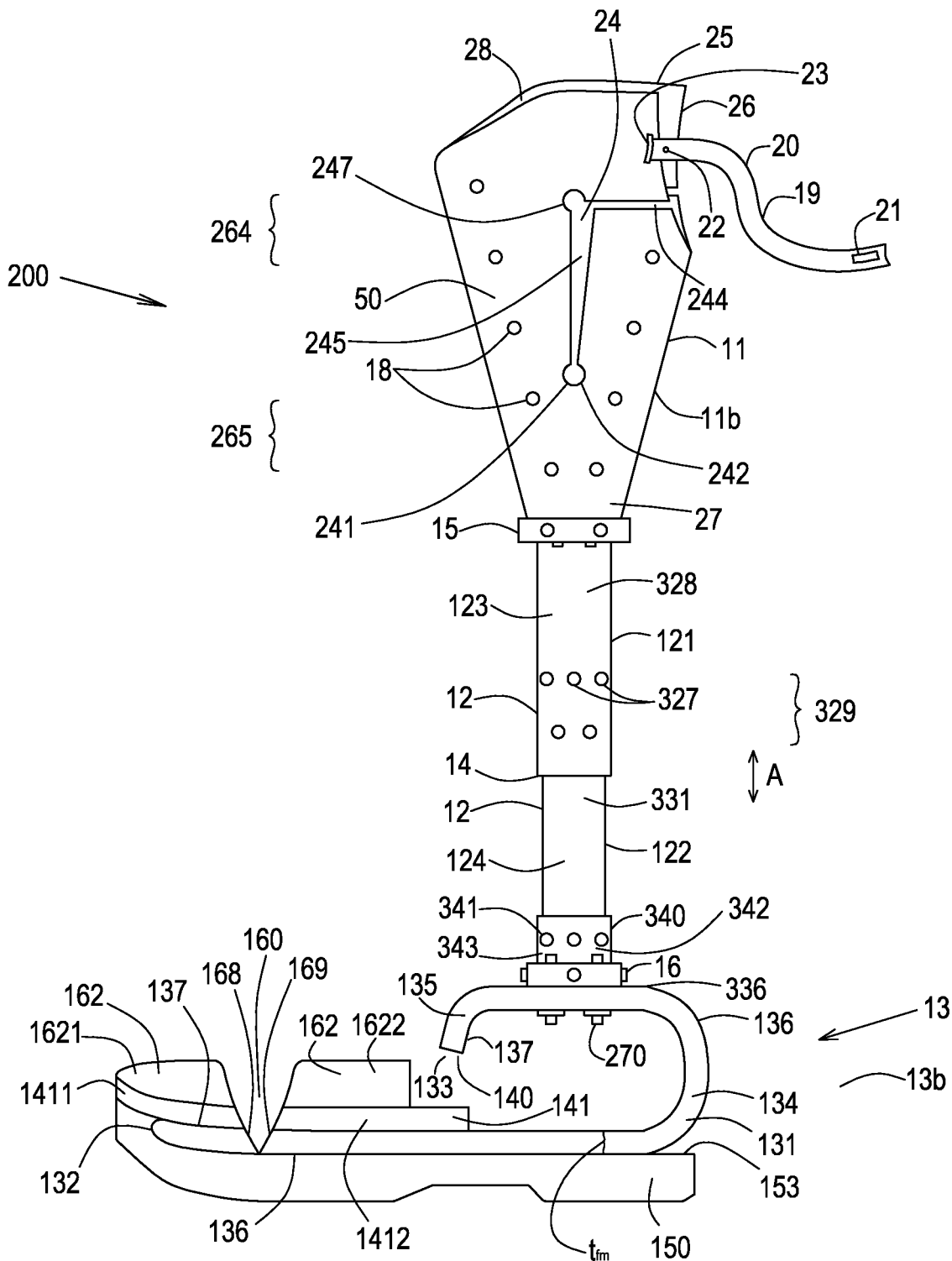

A further exemplary prosthetic device of the present invention is shown in FIG. 1B. As shown in FIG. 1B, exemplary prosthetic device 200 comprises a universal socket 11 (also referred to herein as universal socket 11b) operatively adapted and sized to receive a variety of stump sizes (not shown); an artificial foot 13 (also referred to herein as artificial foot 13b); a rigid member 12 extending from and connecting a second socket end 27 of universal socket 11b to artificial foot member 13b; a socket connector member 15; and a foot connector member 16.

Figure 4A:
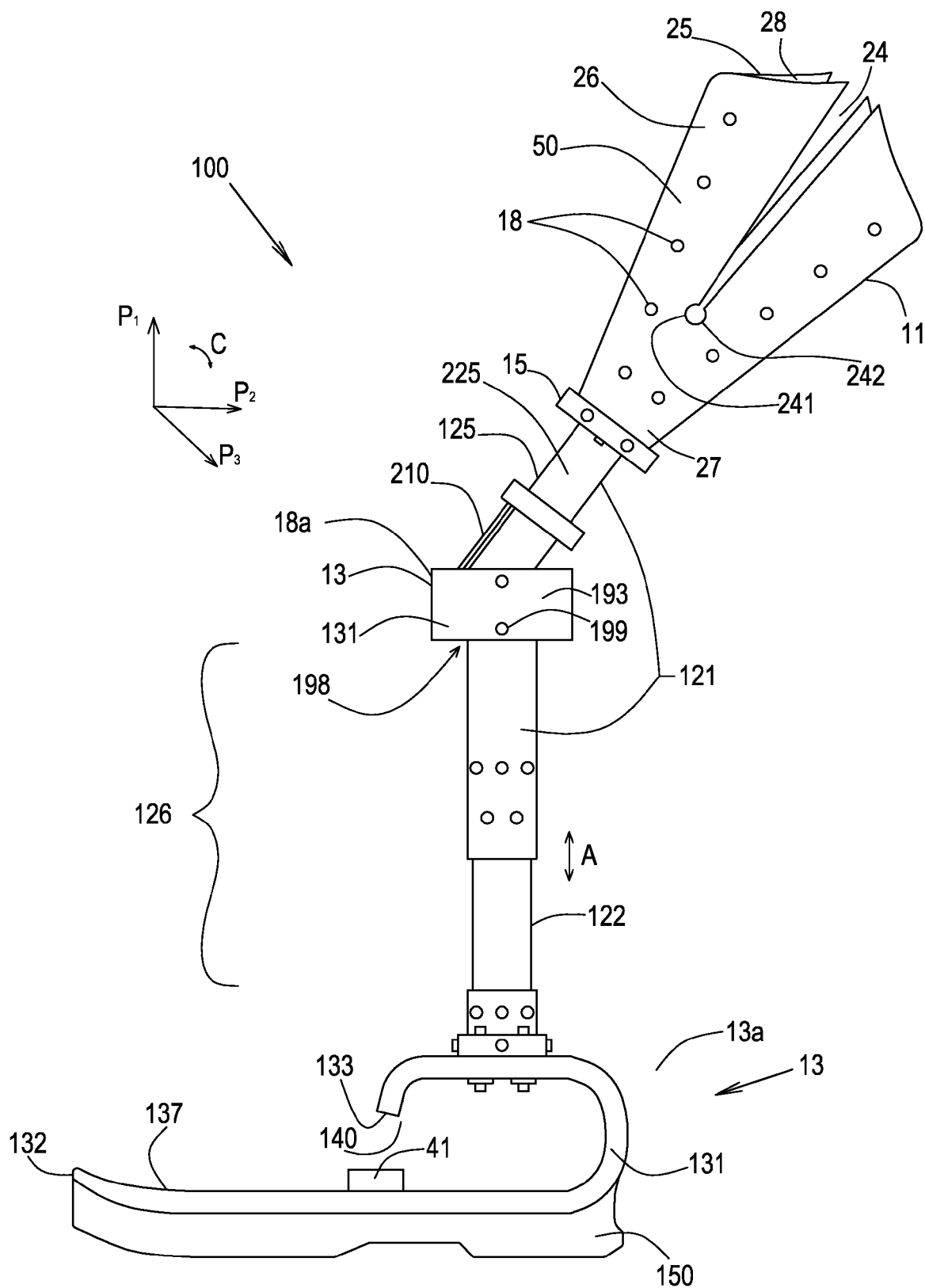
FIGS. 4A-4B depict view of other exemplary prosthetic devices of the present invention.

FIG. 4A depicts another exemplary prosthetic device of the present invention. As shown in FIG. 4A, exemplary prosthetic device 100 comprises a universal socket 11a operatively adapted and sized to receive a variety of stump sizes (not shown); an artificial foot 13a; a rigid member 12 extending from and connecting a second socket end 27 of universal socket 11a to artificial foot member 13a; a socket connector member 15; a foot connector member 16; and an artificial knee 18 (also referred to herein as artificial knee 18a) positioned along rigid member 12.

Figure 4B:
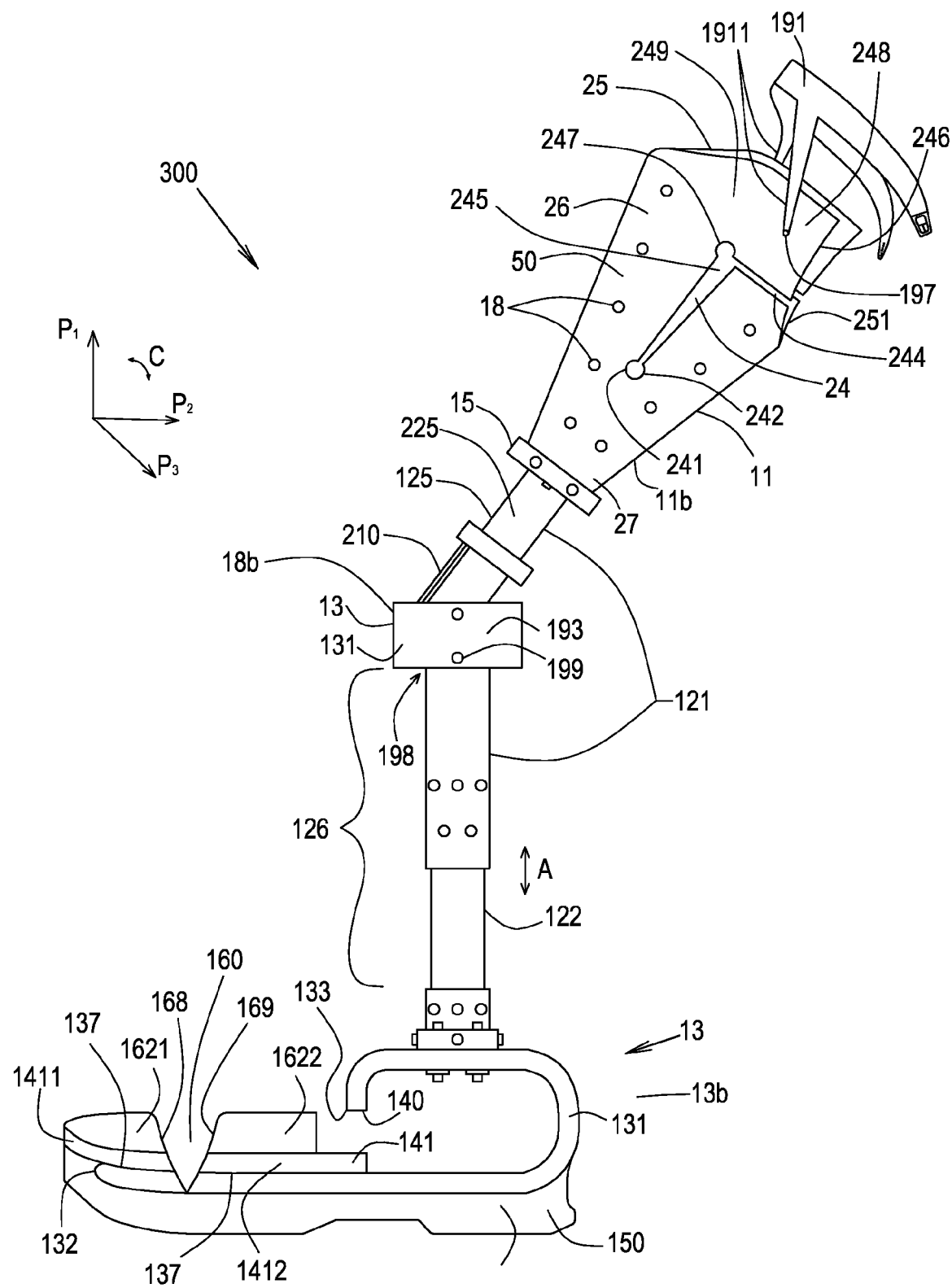

FIG. 4B even further depicts another exemplary prosthetic device of the present invention. As shown in FIG. 4B, exemplary prosthetic device 300 comprises a universal socket 11b operatively adapted and sized to receive a variety of stump sizes (not shown); an artificial foot 13b; a rigid member 12 extending from and connecting a second socket end 27 of universal socket 11b to artificial foot member 13b; a socket connector member 15; a foot connector member 16; and an artificial knee 18 (also referred to herein as artificial knee 18b) positioned along rigid member 12.

I. Prosthetic Devices

As shown in FIGS. 1A-B and 4A-B, prosthetic devices of the present invention may comprise a number of device components and features. A description of various device components and features is provided below.

A. An Artificial Foot

As shown in FIGS. 1A-B and 4A-B, prosthetic devices of the present invention may comprise an artificial foot such as exemplary artificial foot 13a or 13b. As shown in FIG. 1A, exemplary artificial foot 13a comprises a thermoformed foot member 131 having a foot member first end 132, a foot member second end 133 opposite foot member first end 132; at least one foot member curved section 134 (and 135) between foot member first end 132 and foot member second end 133; a foot member outer surface 136 extending between foot member first end 132 to foot member second end 133; a foot member inner surface 137 extending between foot member first end 132 to foot member second end 133; and a foot member thickness $t_{fm}$ extending between foot member outer surface 136 and foot member inner surface 137.

Figure 2A:
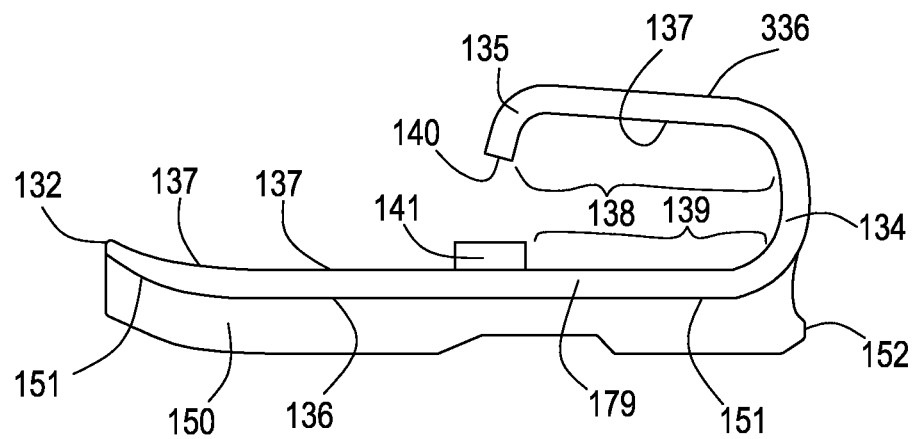
FIGS. 2A-2B depict side views of exemplary artificial feet of the present invention.

As shown, for example, in FIG. 2A, a first portion 138 of foot member inner surface 137 overlaps and faces a second portion 139 of foot member inner surface 137. Further, as shown in FIG. 2A, a foot member second end surface 140 is positioned over and faces foot member inner surface 137. In addition, as shown in FIG. 2A, foot member second end surface 140 is positioned (i) between and connecting foot member outer surface 136 and foot member inner surface 137 to one another and (ii) over and facing foot member inner surface 137. A foot member thickness, $t_{fm}$, is substantially constant from foot member second end surface 140 along the at least one foot member curved section (i.e., foot member curved sections 134 and 135).

It should be noted that foot member thickness $t_{fm}$ may vary along a length of exemplary artificial foot 13, but is typically substantially constant from foot member second end surface 140 along the at least one foot member curved section (i.e., foot member curved sections 134 and 135). In some embodiments, foot member thickness $t_{fm}$ may vary from an average foot member thickness, $t_{fm-ave}$, along a length of exemplary artificial foot 13 from foot member second end surface 140 to just after the at least one foot member curved section (i.e., foot member curved sections 134 and 135) (at, for example, point 179 shown in FIG. 2A) by as much as about ±50% of $t_{fm-ave}$, wherein $t_{fm-ave}$ is calculated as the average thickness of exemplary artificial foot 13 as measured every centimeter along a length of exemplary artificial foot 13 from foot member second end surface 140 to just after the at least one foot member curved section (i.e., foot member curved sections 134 and 135).

Typically, foot member thickness, $t_{fm}$, and average foot member thickness, $t_{fm-ave}$, are both independently less than about 0.8 inches (in) (about 2.0 centimeters (cm)). More typically, foot member thickness, $t_{fm}$, and average foot member thickness, $t_{fm-ave}$ are both independently about 0.5 in (about 1.3 cm).

As shown in FIGS. 1A-4B, exemplary artificial foot 13 comprises (i) a curved heel section 134 having an arc of curvature of from about 160° to about 180°, and (ii) a second end curved section 135 having an arc of curvature of from about 75° to about 90°. Desirably, curved heel section 134 has an arc of curvature of from about 170° to about 180°, and second end curved section 135 has an arc of curvature of from about 85° to about 90°.

As shown in FIGS. 1A-4B, exemplary artificial foot 13 may further comprise a cushioning member 141 positioned along foot member inner surface 137. Exemplary cushioning member 141 is operatively adapted and sized to provide a contact area for foot member second end surface 140 when foot member second end surface 140 is forced into contact with cushioning member 141 (i.e., during walking when exemplary artificial foot 13 contacts a walking surface). As shown in FIG. 3A, desirably, cushioning member 141 has an overall width equal to or greater than an overall width of foot member second end surface 140. Typically, cushioning member 141 has an overall width equal to an overall width of thermoformed foot member 131 along foot member inner surface 137.

Typically, cushioning member 141 has overall dimensions as shown in FIGS. 2B-3B, namely, a width substantially equal to an overall width of exemplary artificial foot 13, and a height and length that are each independently less than about 1.0 in (about 2.5 cm). More typically, cushioning member 141 has a height and length that are each independently about 0.5 in (about 1.3 cm) to about 0.8 in (about 2.0 cm).

As shown in FIGS. 1A-4B, exemplary artificial foot 13 may further comprise a sole member 150 positioned along a lower portion 151 of foot member outer surface 136. Exemplary sole member 150 typically extends a length of exemplary artificial foot 13 from foot member first end 132 to a heel end 152 of exemplary artificial foot 13. In some embodiments, such as shown in FIG. 2A, exemplary sole member 150 extends a length of exemplary artificial foot 13 from foot member first end 132 to heel end 152 without being separated from lower portion 151 of foot member outer surface 136. In other embodiments, such as shown in FIG. 1A, exemplary sole member 150 may extend a length of exemplary artificial foot 13 from foot member first end 132 to heel end 152 and then extend a distance while being separated from foot member outer surface 136 (see, for example, sole member extension portion 153 in FIG. 1A).

Typically, thermoformed foot member 131 comprises a single layer of polymeric material. Suitable polymeric materials for forming thermoformed foot member 131 include, but are not limited to, polyethylene, polypropylene, co-polymers of ethylene and propylene, polyesters, polysilicones, or any combination thereof. In one exemplary embodiment, thermoformed foot member 131 comprises a single layer of continuous polypropylene.

Typically, cushioning member 141, when present, comprises a single layer of polymeric material. Suitable polymeric materials for forming cushioning member 141 include, but are not limited to, CREPE neoprene, polyurethane, silicone rubber, or any combination thereof. In one exemplary embodiment, cushioning member 141 comprises a single layer of continuous CREPE neoprene.

Typically, sole member 150, when present, comprises a single layer of polymeric material. Suitable polymeric materials for forming sole member 150 include, but are not limited to, CREPE neoprene, silicone rubber, or any combination thereof. In one exemplary embodiment, sole member 150 comprises a single layer of continuous CREPE neoprene.

As shown in FIGS. 1B-4B, some artificial feet of the present invention, such as exemplary artificial foot 13b, further comprise a groove 160 extending across a width, $w_{fm}$ (see FIG. 3B), of thermoformed foot member 131 proximate a toe portion of foot member 131. As shown in FIG. 2B, exemplary V-shaped groove 160 (i) extends into foot member inner surface 137 towards foot member outer surface 136, and (ii) is located along foot member 131 between foot member first end 132 and the at least one foot member curved section 134.

Groove 160 extends a depth into foot member 131 from foot member inner surface 137 toward foot member outer surface 136. In some embodiments, groove 160 extends a depth into foot member 131 from foot member inner surface 137 toward foot member outer surface 136, wherein the depth of groove 160 is about 30 to about 100% of a foot member thickness (i.e., $t_{fm}$) on either side of groove 160. Typically, the depth of groove 160 is about 50 to about 100% of a foot member thickness (i.e., $t_{fm}$) on either side of groove 160. Typically, groove 160 extends a depth into foot member 131 from foot member inner surface 137 toward foot member outer surface 136, wherein the depth is substantially equal to the foot member thickness on either side of groove 160 (i.e., is equal to or differs from the foot member thickness on either side of groove 160 by less than 5%). However, in some embodiments, V-shaped groove 160 extends a depth into foot member 131 from foot member inner surface 137 toward foot member outer surface 136, and the depth is less than the foot member thickness on either side of groove 160.

Figure 3A:
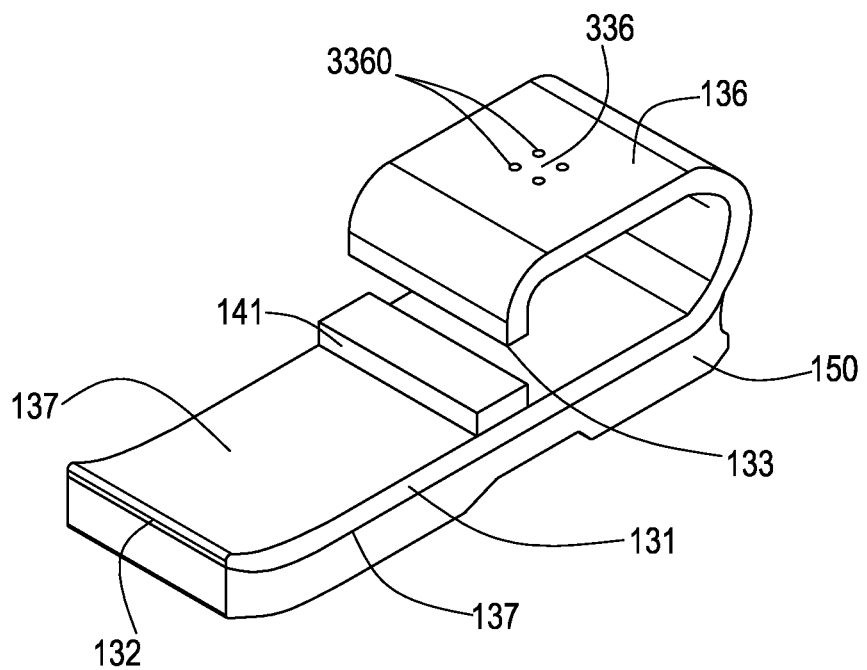
FIGS. 3A-3B depict frontal views of the exemplary artificial feet shown in FIGS. 2A-2B.
Figure 2B:
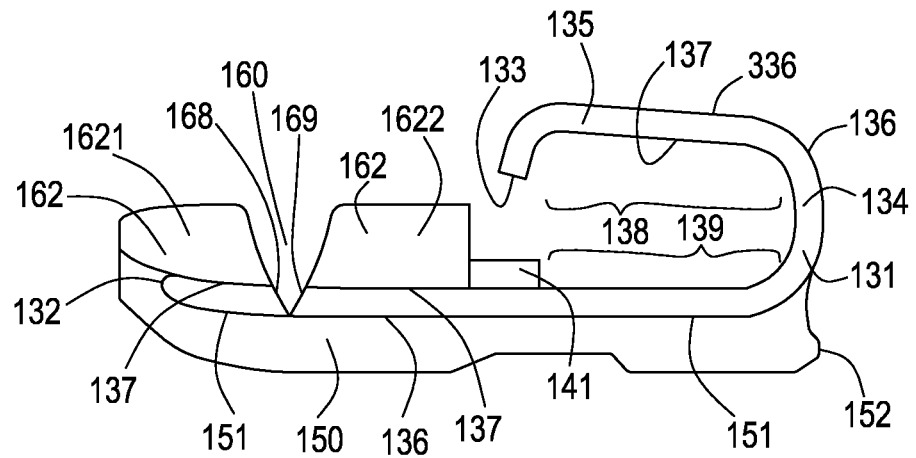
Figure 3B:
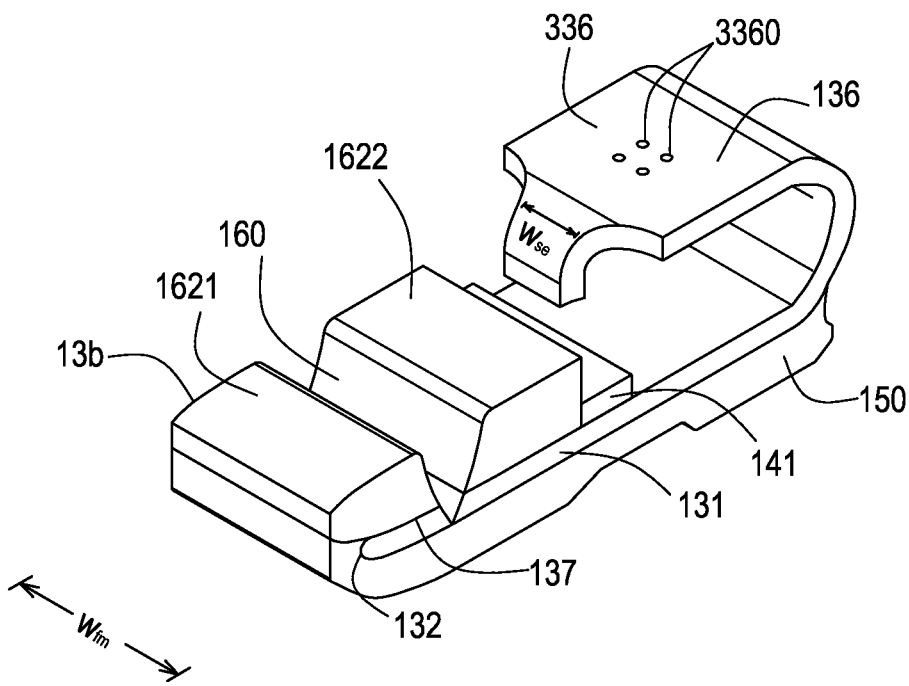

When groove 160 is present, cushioning member 141 may comprise (i) a cushioning member toe portion 1411 and (ii) a cushioning member arch portion 1412 positioned on opposite sides of groove 160 with each independently extending across a width ($w_{fm}$) of foot member 131 on opposite sides of V-shaped groove 160 as shown in FIG. 1B. In other embodiments, when groove 160 is present, cushioning member 141 comprises a single cushioning member 141 positioned beneath foot member second end surface 140 and extending across a width ($w_{fm}$) of foot member 131 as shown in FIGS. 2B and 3B. Typically, cushioning member 141 (and cushioning member toe portion 1411 and cushioning member arch portion 1412) extends across a full width ($w_{fm}$) of foot member 131; however, in some embodiments, cushioning member 141 (and cushioning member toe portion 1411 and cushioning member arch portion 1412) may extend across less than the full width ($w_{fm}$) of foot member 131.

As shown in FIGS. 1B-4B, some artificial feet of the present invention, such as exemplary artificial foot 13b, may further comprise an upper foot member such as an upper foot member 162. Upper foot member 162 may be positioned over at least a portion of (i) cushioning member 141 (i.e., as shown in FIG. 1B), (ii) thermoformed foot member 131 (i.e., along foot member inner surface 137 at point 165 as shown in FIGS. 2B and 3B), or (iii) both (i) and (ii). In some embodiments, upper foot member 162 is positioned over at least a portion of thermoformed foot member 131 (as shown in FIGS. 2B and 3B). In some embodiments, upper foot member 162 is positioned over at least a portion of cushioning member 141 (as shown in FIG. 1B). In other embodiments, upper foot member 162 is positioned over at least a portion of (i) cushioning member 141 and (ii) thermoformed foot member 131.

When groove 160 and upper foot member 162 are both present, upper foot member 162 may comprise (i) an upper foot member toe portion 1621 and (ii) an upper foot member arch portion 1622 positioned on opposite sides of groove 160 with each independently extending across a width ($w_{fm}$) of foot member 131 on opposite sides of groove 160 as shown in FIGS. 1B and 4B)

When present, upper foot member 162 (i.e., upper foot member 162, upper foot member toe portion 1621 and/or upper foot member arch portion 1622) typically comprises a single layer of continuous CREPE neoprene. Typically, the single layer of continuous CREPE neoprene forming upper foot member 162 (i.e., upper foot member 162, upper foot member toe portion 1621 and/or upper foot member arch portion 1622) has a hardness (i.e., as measured using, for example, standard test method ASTM D2240) that is less than a hardness for the single layer of continuous CREPE neoprene forming sole member 150.

It should be understood that although groove 160 is shown as having a V-shape with substantially straight opposing groove walls 168 and 169 (see, FIG. 4B), a groove having any other groove configuration may be used in place of V-shaped groove 160 as long as the groove enables thermoformed foot member 131 to bend such that opposing walls/surfaces 168 and 169 move towards one another. For example, opposing walls 168 and 169 may have any curved configuration (e.g., opposing walls have a concave and a convex configuration). In other embodiments, groove 160 may have a shape other than a V-shape, for example, a circular shape, a square shape, etc., as long as opposing walls 168 and 169 within groove 160 can move towards one another.

Further, it should be noted that the width ($w_{fm}$) of foot member 131 may vary along a length of foot member 131. For example, as shown in FIG. 3A, foot member 131 has a width ($w_{fm}$) that is substantially the same along a length of foot member 131 (e.g., from foot member first end 132 to foot member second end 133). In other embodiments, such as shown in FIG. 3B, foot member 131 may have a width ($w_{fm}$) that varies along a length of foot member 131 (e.g., from foot member first end 132 to foot member second end 133). In one desired embodiment, as shown in FIG. 3B, foot member 131 has a width ($w_{fm}$) that varies along a length of foot member 131 (e.g., from foot member first end 132 to foot member second end 133) with a narrowest width, $w_{se}$, proximate foot member second end 133.

B. An Artificial Knee

As shown in FIGS. 4A and 4B, prosthetic devices of the present invention may comprise an artificial knee such as exemplary artificial knee 18 (e.g., 18a, 18b or 18c). As shown in FIGS. 4A and 4B, exemplary artificial knee 18 (e.g., 18a, 18b or 18c) may be positioned along upper rigid member 121 so as to separate rigid member 12 into an above-knee portion 125 and a below-knee portion 126 of rigid member 12.

Figure 5A:
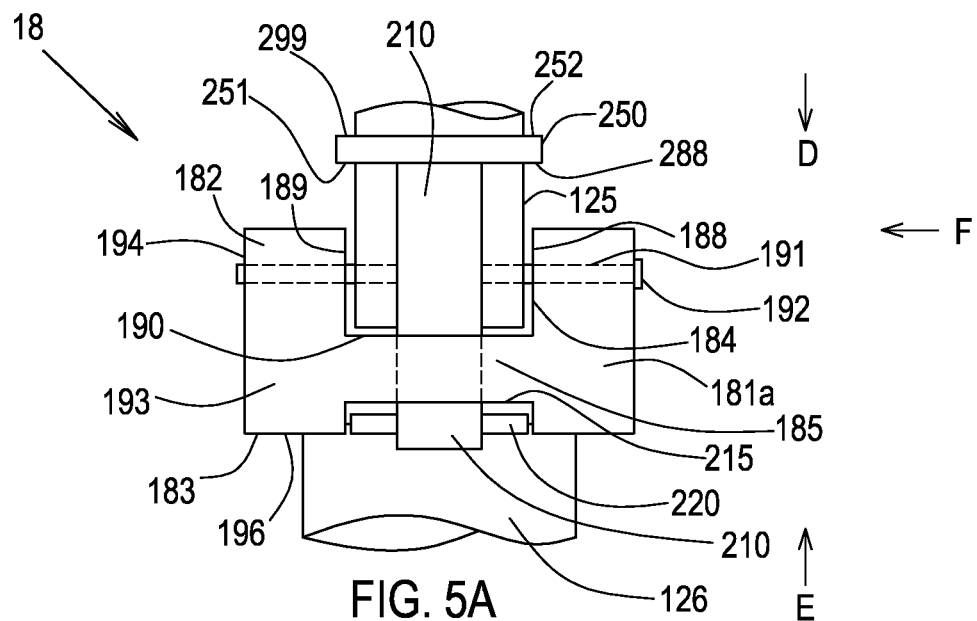
FIGS. 5A-5C depict frontal views of exemplary artificial knees of the present invention.

As shown in FIGS. 5A-10, exemplary artificial knee 18 (e.g., 18a, 18b or 18c) comprises numerous features. As shown in FIGS. 5A, 5B and 5C, exemplary artificial knee 18 (i.e., 18a, 18b and 18c) comprises artificial knee member 181 (i.e., 181a, 181b and 181c) having (i) an upper end 182 configured to be attachable to above-knee portion 125 of rigid member 12; (ii) a lower end 183 configured to be attachable to below-knee portion 126 of rigid member 12; and (iii) a channel 184 extending along upper end 182 and through artificial knee member 181 (i.e., 181a, 181b and 181c) from a front portion 185 (see, FIGS. 6A, 6B and 6C) to a rear portion 186 of artificial knee member 181 (i.e., 181a, 181b and 181c). Channel 184 has a channel surface 187 forming opposite channel side surfaces 188 and 189, and a channel floor surface 190 positioned between opposite channel side surfaces 188 and 189.

Figure 6A:
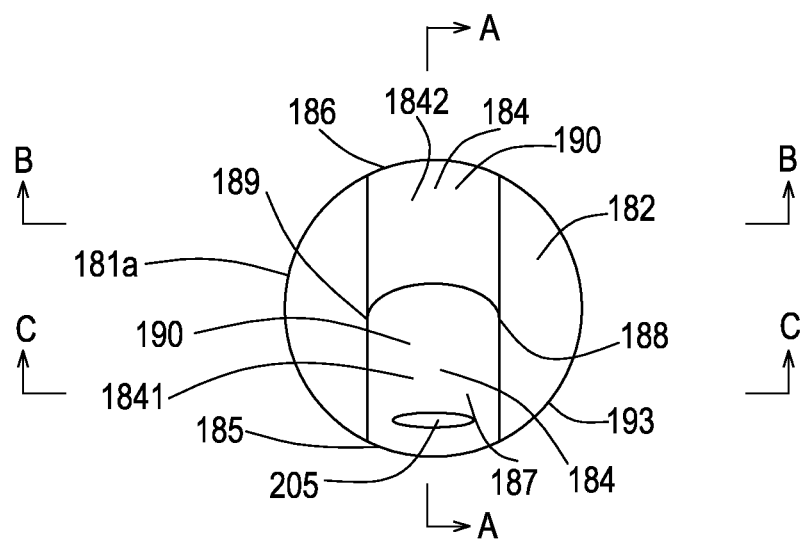
FIGS. 6A-6C depict a top views of the exemplary artificial knee members shown in FIGS. 5A-5C, respectively, as viewed along direction line D.
Figure 7A:
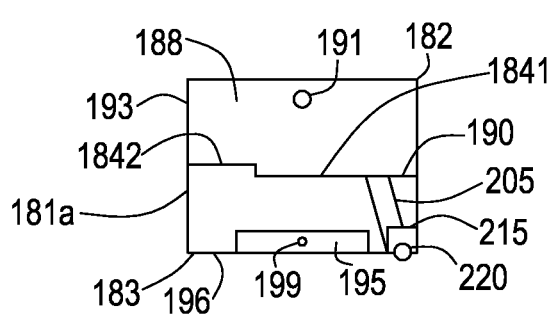
FIGS. 7A-7C depict cross-sectional side views of the exemplary artificial knee members shown in FIGS. 6A-6C, respectively, as viewed along line A-A.
Figure 6B:
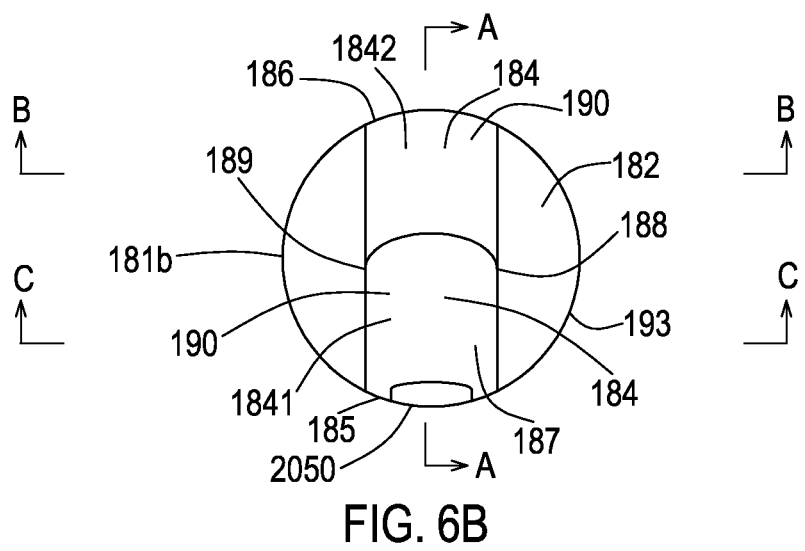
Figure 7B:
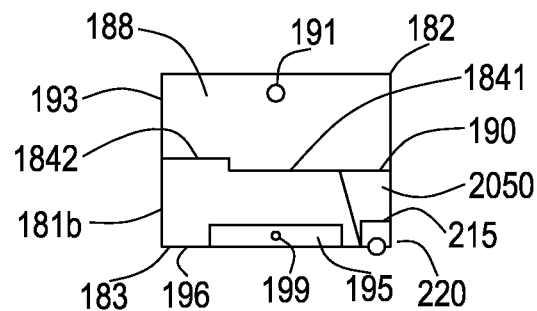
Figure 6C:
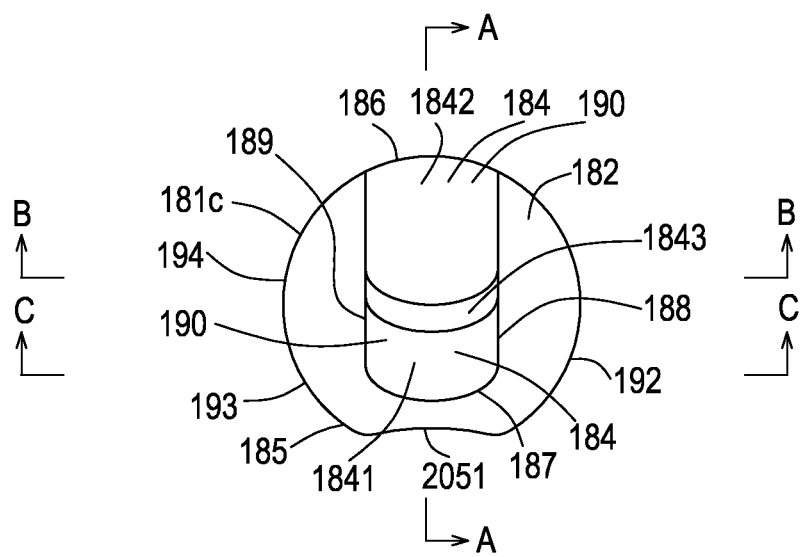
Figure 7C:
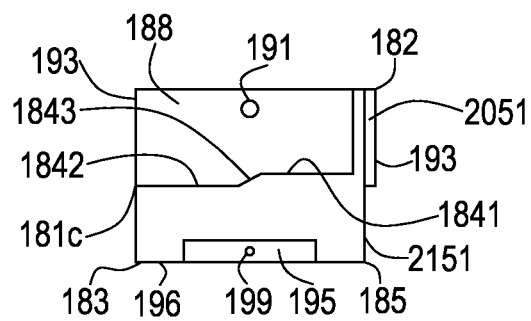
Figure 8A:
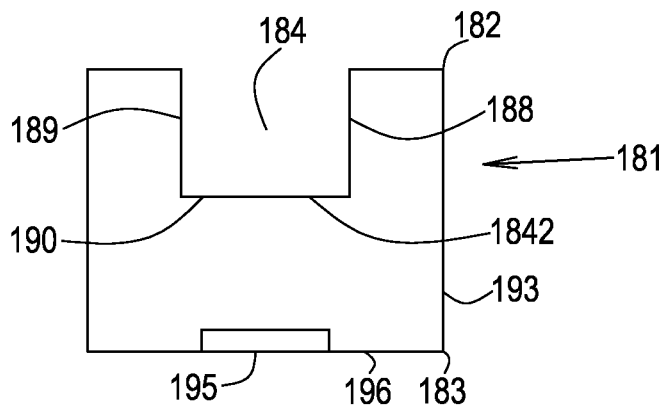
FIG. 8A depicts a cross-sectional frontal view of the exemplary artificial knee member shown in FIGS. 6A-6B as viewed along line B-B.
Figure 9A:
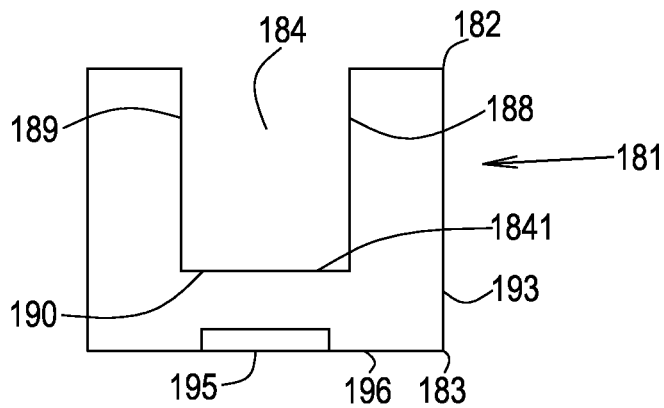
FIG. 9A depicts a cross-sectional frontal view of the exemplary artificial knee member shown in FIG. 6A-6B as viewed along line C-C.
Figure 10A:
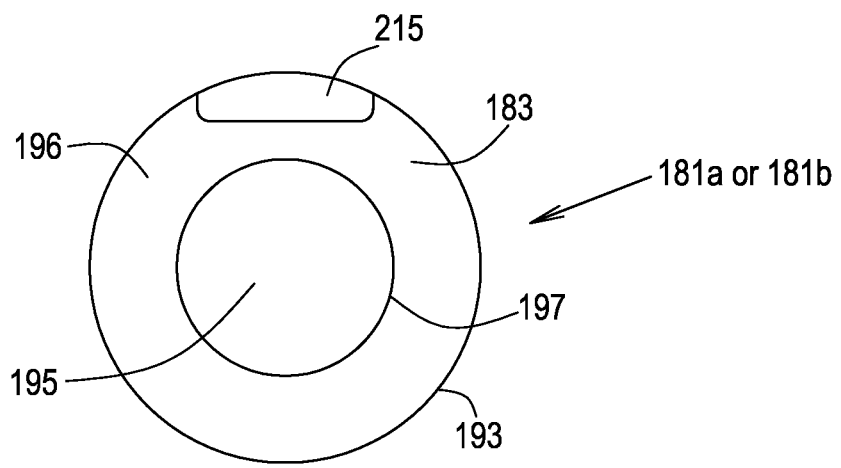
FIG. 10A depicts a bottom view of the exemplary artificial knee member shown in FIG. 5A or FIG. 5B as viewed along direction line E.
Figure 8B:
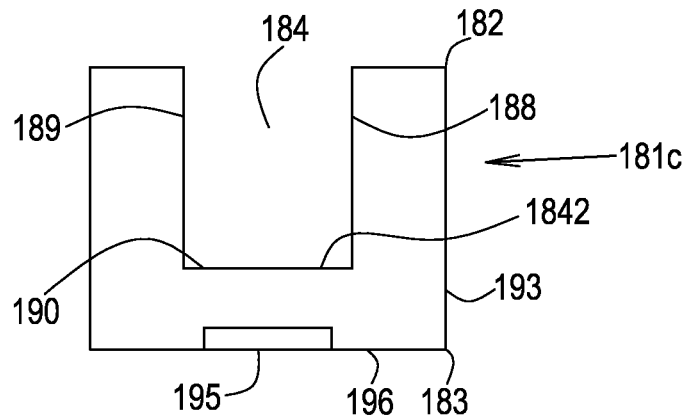
FIG. 8B depicts a cross-sectional frontal view of the exemplary artificial knee member shown in FIG. 6C as viewed along line B-B.
Figure 9B:
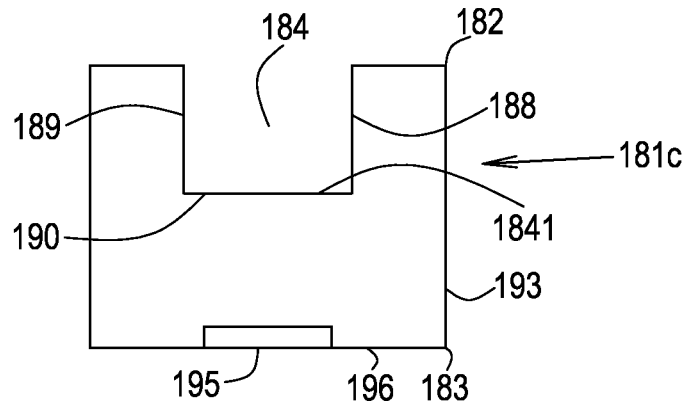
FIG. 9B depicts a cross-sectional frontal view of the exemplary artificial knee member shown in FIG. 6C as viewed along line C-C.
Figure 10B:
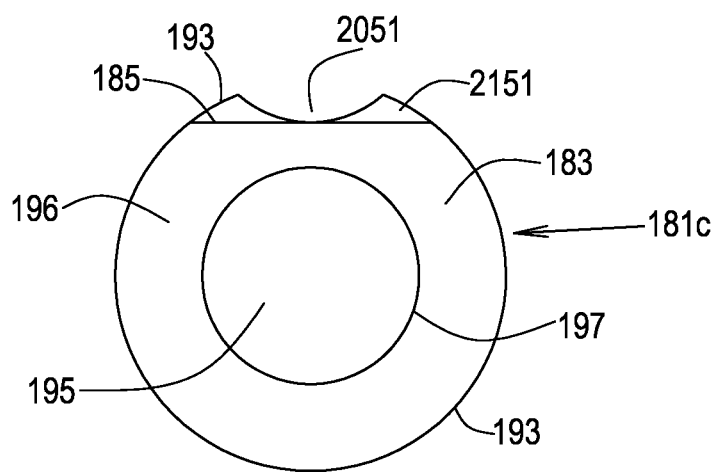
FIG. 10B depicts a bottom view of the exemplary artificial knee member shown in FIG. 5C as viewed along direction line E.

As shown in FIGS. 6A-9, channel 184 of exemplary artificial knee 18 (i.e., 18a, 18b and 18c) may have a complex configuration comprising two distinct areas represented by (i) a forward channel 1841 cross-sectional configuration and (ii) a rear channel 1842 cross-sectional configuration (shown separated by a ramp area 1843 therebetween in FIGS. 6C and 7C). The complex configuration enables an end 226 of above-knee portion 125 of rigid member 12 (i.e., shown in FIG. 11) to sit flush along channel surface 187 of forward channel 1841 cross-sectional configuration when exemplary artificial knee 18 (i.e., 18a, 18b and 18c) is in a "relaxed state" (i.e., above-knee portion 125 of rigid member 12 extends substantially upward in direction $P_1$ as shown in FIGS. 4A and 4B). The complex configuration also enables an outer surface 225 along rear portion 269 of above-knee portion 125 of rigid member 12 (i.e., shown in FIG. 11) to have contact with channel surface 187 of rear channel 1842 cross-sectional configuration when exemplary artificial knee 18 (i.e., 18a, 18b and 18c) is in a "maximum tensioned state" (i.e., above-knee portion 125 of rigid member 12 extends substantially horizontally in direction $P_2$ or beyond a horizontal position in direction $P_3$ as shown in FIGS. 4A and 4B).

Figure 5B:
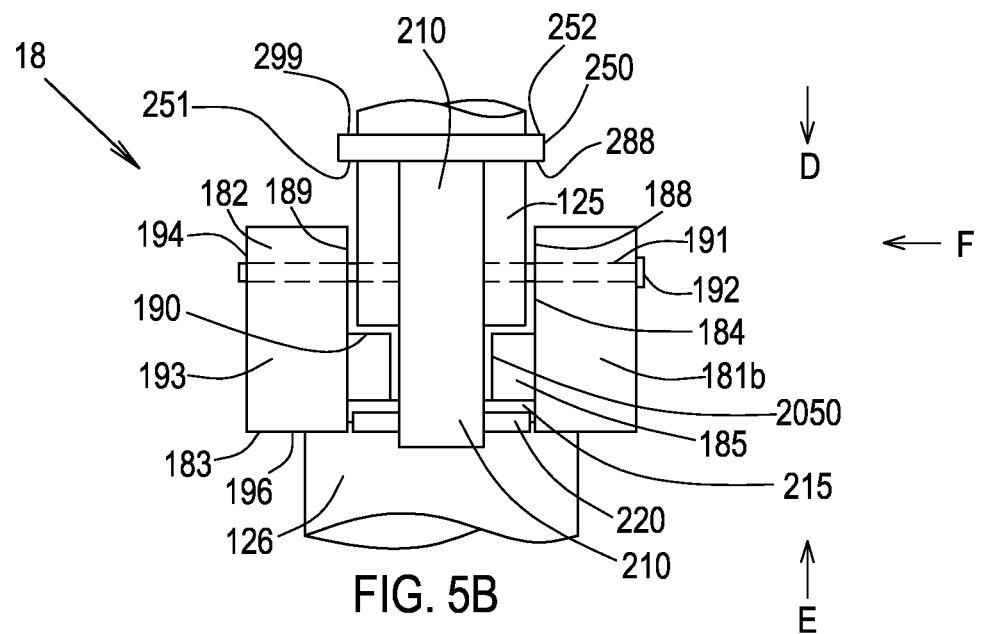
Figure 5C:
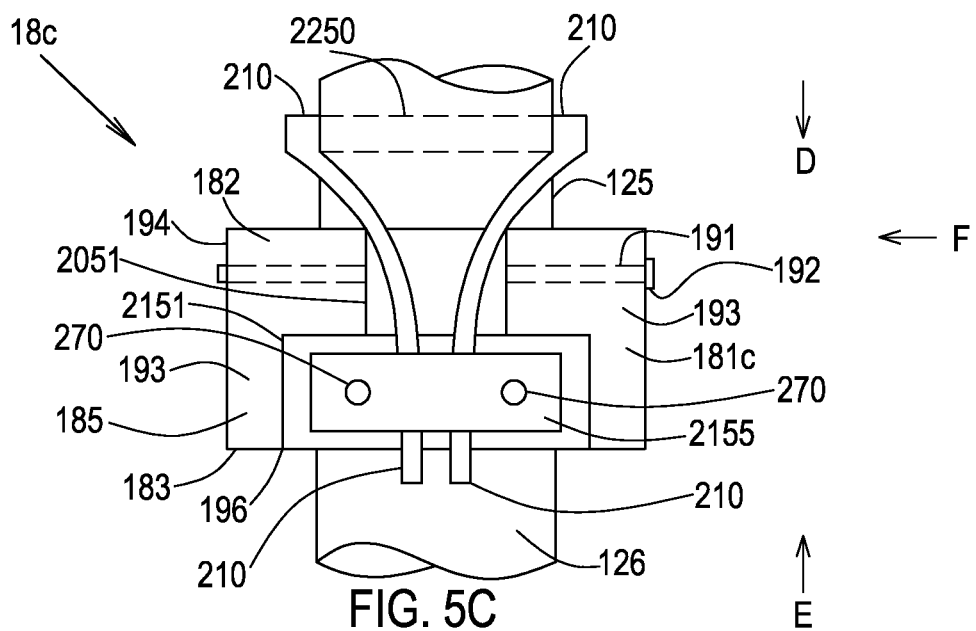

As shown in FIGS. 5A, 5B and 5C, exemplary artificial knee 18 (i.e., 18a, 18b and 18c) may further comprise a horizontally extending connecting hole 191 extending through upper portion 182 of artificial knee member 181 (i.e., 181a, 181b and 181c). Horizontally extending connecting hole 191 extends from a first portion 192 of an outer peripheral surface 193 of artificial knee member 181 (i.e., 181a, 181b and 181c), out of one channel side surface (e.g., channel side surface 188), through channel 184, into an opposite channel side surface (e.g., channel side surface 189), and out of a second portion 194 of outer peripheral surface 193 of artificial knee member 181 (i.e., 181a, 181b and 181c) opposite first portion 192 of outer peripheral surface 193 of artificial knee member 181 (i.e., 181a, 181b and 181c). As discussed below, a pin or bolt (not shown) extends through (i) horizontally extending connecting hole 191 and (ii) hole 228 within above-knee portion 125 of rigid member 12 as shown in FIG. 11.

As shown in FIGS. 7A-10, exemplary artificial knee 18 (i.e., 18a, 18b and 18c) may further comprise a centrally located hollow portion 195 extending into a lower surface 196 of lower end 183. Desirably, centrally located hollow portion 196 has a hollow portion cross-sectional area 197 corresponding to an outer cross-sectional area (not shown) of a connecting portion 198 of below-knee portion 126 of rigid member 12. Exemplary artificial knee 18 (i.e., 18a, 18b and 18c) may further comprise a set of horizontally extending holes 199 extending from outer peripheral surface 193 of artificial knee member 181 (i.e., 181a, 181b and 181c) to centrally located hollow portion 195, wherein each hole 199 is sized to accommodate a fastener (e.g., exemplary fastener 270 comprising threads 271 shown in FIG. 14) within a set of similar or identical fasteners (e.g., a set of similar or identical fasteners such as screws).

As shown in FIGS. 6A and 7A, exemplary artificial knee 18a may further comprise a tensioning member channel 205 extending through artificial knee member 181a from channel floor surface 190 to a cut-out section 215 along front portion 185 of lower end 183. In addition, as shown in FIG. 5A, exemplary artificial knee 18a may further comprise a tensioning member 210 (i) positioned within and thru tensioning member channel 205 and (ii) connecting front portion 185 of lower end 183 to above-knee portion 125 of rigid member 12.

In another embodiment as shown in FIGS. 6B and 7B, exemplary artificial knee 18b may further comprise a tensioning member groove 2050 extending through artificial knee member 181b from channel floor surface 190 to a cut-out section 215 along front portion 185 of lower end 183. In addition, as shown in FIG. 5B, exemplary artificial knee 18b may further comprise a tensioning member 210 (i) positioned within and along tensioning member groove 2050 and (ii) connecting front portion 185 of lower end 183 to above-knee portion 125 of rigid member 12.

As shown in FIGS. 5A-5B and 7A-7B, exemplary artificial knee 18 (i.e., 18a and 18b) may further comprise a first tensioning member positioning/securing member 220 positioned within cut-out section 215. Exemplary first tensioning member positioning/securing member 220 shown in FIGS. 5A-5B and 7A-7B comprises a roller that extends from one side surface 298 to an opposite side surface 299 of cut-out section 215. A second tensioning member positioning/securing member 250 may be positioned along above-knee portion 125 of rigid member 12. Although shown in the figures, second tensioning member positioning/securing member 250 may have a configuration similar to lower end 183 and tensioning member channel 205 (or tensioning member groove 2050), wherein a second tensioning member channel (or groove) extends through second tensioning member positioning/securing member 250 from a lower surface 251 to an upper surface 252 of second tensioning member positioning/securing member 250.

In another embodiment as shown in FIGS. 6C and 7C, exemplary artificial knee 18c may further comprise a tensioning member groove 2051 extending through artificial knee member 181c from upper end 182 to a cut-out section 2151 along front portion 185 of lower end 183. In addition, as shown in FIG. 5C, exemplary artificial knee 18c may further comprise a tensioning member 210 (i) extending through hole 2250 of above-knee portion 125 of rigid member 12 (see also, FIG. 11B), (ii) positioned within and along tensioning member groove 2051, (iii) clamped onto a cut-out portion 2151 of artificial knee member 181c via clamp member 2155 and fasteners 270, and (iv) connecting front portion 185 of lower end 183 to above-knee portion 125 of rigid member 12.

Figure 18A:
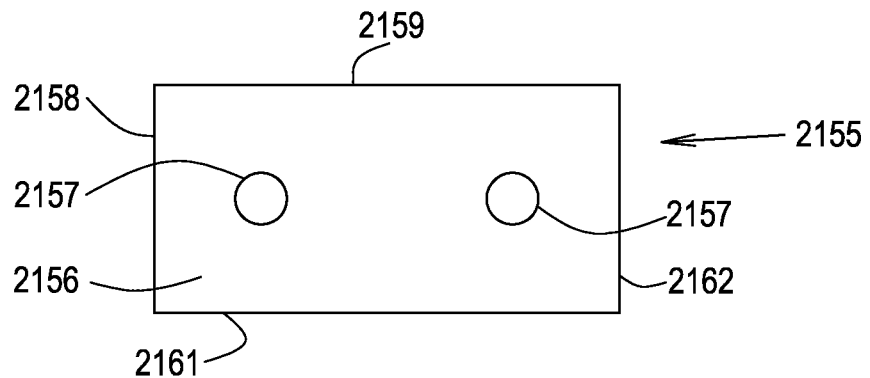
FIGS. 18A-C depict various views of the exemplary clamp member shown in FIG. 5C.
Figure 18B:
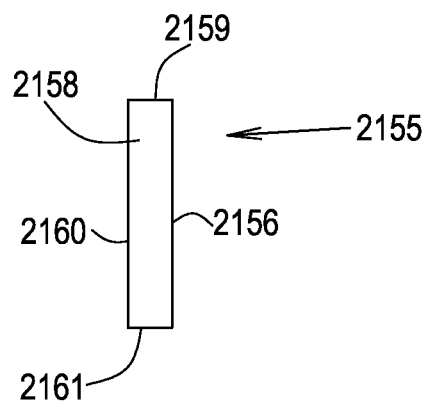
Figure 18C:
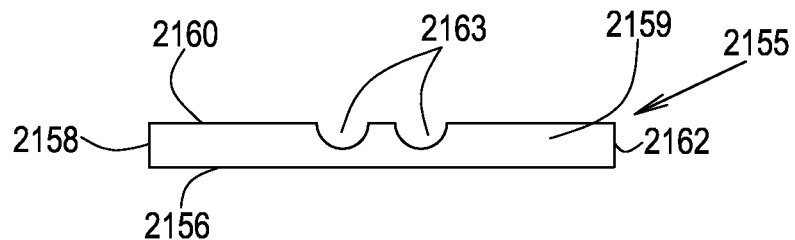

FIGS. 18A-18C provide front, side and top views of exemplary clamp member 2155. As shown in FIG. 18A, exemplary clamp member 2155 comprises a front surface 2156 with holes 2157 extending therethrough, top surface 2159, bottom surface 2161, and opposite side surfaces 2158 and 2162. As shown in FIG. 18B, exemplary clamp member 2155 also comprises rear surface 2160. As shown in FIG. 18C, exemplary clamp member 2155 may also comprises one or more indentations 2163 within rear surface 2160. Indentations 2163, when present, (i) may extend a full length of clamp member 2155 from top surface 2159 to bottom surface 2161, and (ii) may provide an area in which to position portions of tensioning member 210 (e.g., surgical tubing). It should be noted that in other embodiments (not shown), rear surface 2160 does not comprise any indentations 2163 within rear surface 2160 (i.e., rear surface 2160 is substantially flat or planar).

Exemplary tensioning member 210 may comprise any tension-providing material. Suitable tensioning-providing materials include, but are not limited to, a bungee cord type material, surgical tubing, a spring, any other elastic material, or a combination thereof. In one desired embodiment, exemplary tensioning member 210 comprises an elastic band material such as a rubber band. In another desired embodiment (shown in FIG. 5C), exemplary tensioning member 210 comprises surgical tubing.

Exemplary artificial knee 18 (i.e., 18a, 18b and 18c) enables controlled bending of rigid member 12 at artificial knee member 181 (i.e., 181a, 181b and 181c). Typically, artificial knee member 181 (i.e., 181a, 181b and 181c) enables controlled bending of rigid member 12 of about 90° in a direction as shown by arrow C and as shown by position $P_1$ and position $P_2$ in FIGS. 4A and 4B. However, in some embodiments, artificial knee member 181 (i.e., 181a, 181b and 181c) may enable controlled bending of rigid member 12 of greater than 90° (e.g., any angle between 90° and up to about 135°, typically, about 110° in a direction as shown by arrow C and as shown by position $P_1$ and position $P_3$ in FIGS. 4A and 4B. Typically, rigid member 12 is configured to remain in a straight configuration at artificial knee member 181 (i.e., 181a, 181b and 181c), and a desired amount of tension is necessary to move rigid member 12 into an angled configuration (e.g., in position $P_2$ or position $P_3$) via tensioning member 210. In exemplary prosthetic devices 100 and 300 shown in FIGS. 4A and 4B, artificial knee member 181 (i.e., 181a, 181b and 181c) comprises tensioning member 210 that keeps rigid member 12 in a straight configuration (i.e., in position $P_1$) at artificial knee member 181 (i.e., 181a, 181b and 181c) when in a relaxed state.

As shown in FIGS. 4A and 4B, artificial knee member 181 (i.e., 181a, 181b and 181c) is attachable to a socket, such as exemplary universal socket 11 (i.e., 11a and 11b), via above-knee portion 125 of rigid member 12, while below-knee portion 126 of rigid member 12 is attachable to an artificial foot (e.g., artificial foot member 13a or 13b). Further, although not shown in FIGS. 4A and 4B, each of above-knee portion 125 and below-knee portion 126 of rigid member 12 may independently comprise a length adjustment/locking mechanism, such as exemplary length adjustment/locking mechanism 14 described below, so as to independently adjust and securely fix a length of each of above-knee portion 125 and below-knee portion 126.

C. A Socket

As shown in FIGS. 1A-B and 4A-B, exemplary prosthetic devices 10, 100, 200 and 300 may further comprise a socket such as exemplary universal socket 11 (i.e., 11a and 11b). Exemplary universal socket 11 (i.e., 11a and 11b) is operatively adapted and sized to receive a variety of stump sizes (not shown). Exemplary universal socket 11 (i.e., 11a and 11b) comprises a first socket open end 25 sized to receive a user stump (not shown), and a second socket end 27 opposite the first socket end 25. Exemplary universal socket 11 (i.e., 11a and 11b) further comprises at least two differently sized socket regions positioned between first socket open end 25 and second socket end 27, wherein the at least two differently sized socket regions comprise an upper socket region 264 proximate first socket open end 25 and a lower socket region 265 positioned between upper socket region 264 and second socket end 27. Upper socket region 264 has an upper region cross-sectional area, lower socket region 265 has a lower region cross-sectional area, and the upper region cross-sectional area is greater than the lower region cross-sectional area.

Exemplary prosthetic devices 10, 100, 200 and 300 further comprise at least one slot 24 (i.e., 24a and 24b) extending from first socket open end 25 towards second socket end 27. The at least one slot 24 (i.e., 24a and 24b) may extend into lower socket region 265 (i.e., near second socket end 27). Typically, the at least one slot 24 (i.e., 24a and 24b) comprises two slots on opposite sides of the universal socket 11 (i.e., 11a and 11b). However, it should be noted that in some embodiments, only one slot 24 (i.e., 24a and 24b) is needed in a given exemplary prosthetic device.

Exemplary prosthetic device 10 further comprises one or more openings 18 extending through a side wall 50 of the universal socket 11 (i.e., 11a and 11b) from an outer surface 26 to an inner surface 28 of the universal socket 11 (i.e., 11a and 11b). One or more openings 18 provide desired air flow through universal socket 11 (i.e., 11a and 11b), as well as added traction between universal socket 11 (i.e., 11a and 11b) and a user's stump (not shown).

Exemplary prosthetic device 10 further comprises one or more tightening elements operatively adapted to tighten the universal socket 11 (i.e., 11a and 11b) onto a user's stump positioned within the universal socket 11 (not shown). In one exemplary embodiment, and as shown in FIGS. 1A and 4A, the one or more tightening elements comprise one or more straps 19 extending along an outer surface 26 of the universal socket 11 (i.e., 11a and 11b). Each strap may desirably have (i) a length so as to be capable of extending along an outer perimeter of the universal socket 11 (i.e., 11a and 11b), and (ii) at least one fastening component that enables one portion of the strap (i.e., 20) to attach to another portion of the strap (i.e., 21). For example, the at least one fastening component may comprise hook and loop material (i.e., 20, 21). Each strap 19 may be attached to an outer surface 26 of the universal socket 11 (i.e., 11a and 11b) via a strap attachment member 22. The universal socket 11 (i.e., 11a and 11b) may further comprise one or more strap loops 23 positioned along the outer surface 26 of universal socket 11 (i.e., 11a and 11b) in order to control a position of a given strap 19 along the outer surface 26 of universal socket 11 (i.e., 11a and 11b).

It should be noted that any tightening element(s) may be used to tighten the universal socket 11 (i.e., 11a and 11b) onto a user's stump positioned within the universal socket 11 (not shown). Suitable tightening elements include, but are not limited to, male/female clasping devices positioned on either side of at least one slot 24 (i.e., 24a and 24b) (e.g., clasping devices typically used on ski boots or roller blades); rubber or other elastomeric band materials that extend around a perimeter of universal socket 11 (i.e., 11a and 11b); hook and loop material in combination with one or more clasps positioned on either side of at least one slot 24 (i.e., 24a and 24b) (e.g., the hook and loop material does not extend completely around universal socket 11 (i.e., 11a and 11b)); or any combination of one or more types of tightening elements.

Figure 17A:
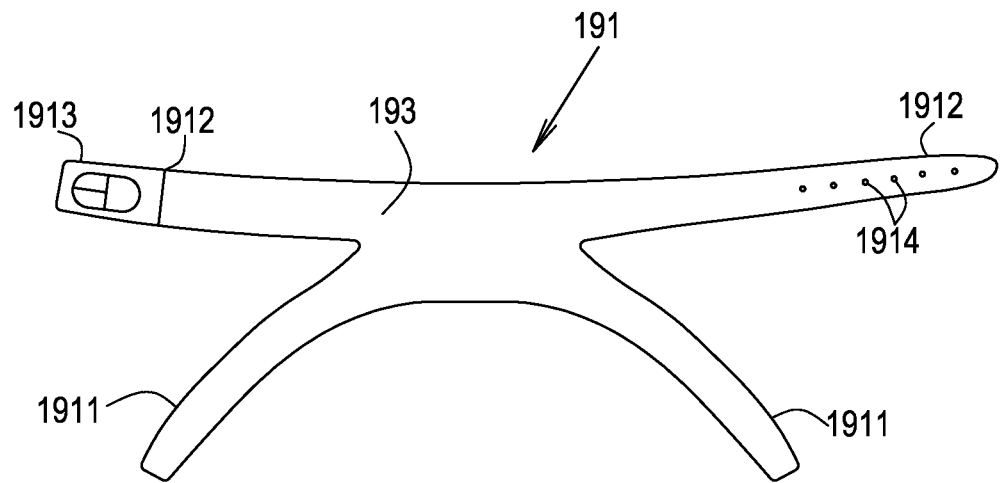
FIGS. 17A-B depict opposite side views of the exemplary strap shown in FIG. 4B.
Figure 17B:
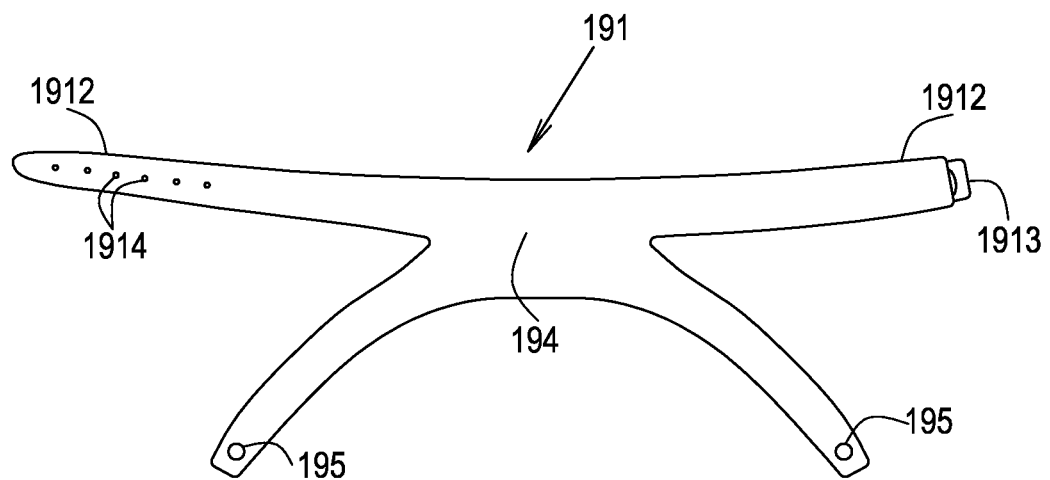

In some embodiments, a strap as shown in FIG. 4B, and more detailed in FIGS. 17A-B, may be used to connect a universal socket onto a user's stump. As shown in FIGS. 17A-B, exemplary strap 191 has (i) a first connector portion 1911 that extends along an outer surface of a universal socket (e.g., universal socket 11b shown in FIG. 4B) so as to attach to the outer surface of the universal socket (e.g., outer surface 26 of universal socket 11b shown in FIG. 4B), and (ii) and a second connector portion 1912 having a first strap portion 1913 having one or more male connectors (e.g., a bucket) positioned along a length of first strap portion 1913 and a second strap portion 1914 opposite first strap portion 1913, wherein second strap portion 1914 comprising one or more female connectors (e.g., holes for bucket) positioned along a length of second strap portion 1914, the one or more female connectors 1914 being connectable to one or more male connectors 1913 so as to surround at least a portion of a user's leg (not shown). Typically, second strap portion 1914 surrounds at least a portion of a user's leg (not shown) above the user's knee.

As shown in FIGS. 17A-B, exemplary strap 191 has an outer surface 193, an inner surface 194, and one or more connectors 195 positioned along inner surface 194. One or more connectors 195 are operatively adapted and sized to connect to corresponding connectors along an outer surface of a universal socket (e.g., outer surface 26 of universal socket 11b shown in FIG. 4B). See, for example, exemplary strap 191 as shown in FIG. 4B.

As shown in FIGS. 1B and 4B, in some embodiments, the universal socket (e.g., exemplary universal socket 11b) may comprise one or more additional features such as (1) a first circular slot component 241 at a slot end 242 opposite first socket open end 25; (2)(i) a horizontal slot component 244 within upper socket region 264, and (ii) a vertical slot component 245 extending from horizontal slot component 244 towards lower socket region 265; and/or (3) a second circular slot component 247 at an intersection between horizontal slot component 244 and vertical slot component 245. In some embodiments, the universal socket (e.g., exemplary universal socket 11b) comprises first circular slot component 241 at a slot end 242 opposite first socket open end 25. In some embodiments, the universal socket (e.g., exemplary universal socket 11b) comprises (i) horizontal slot component 244 within upper socket region 264, and (ii) a vertical slot component 245 extending from horizontal slot component 244 towards lower socket region 265. In some embodiments, the universal socket (e.g., exemplary universal socket 11b) comprises second circular slot component 247 at an intersection between horizontal slot component 244 and vertical slot component 245. In some embodiments, the universal socket (e.g., exemplary universal socket 11b) comprises first circular slot component 241 at a slot end 242 opposite first socket open end 25. In some embodiments, the universal socket (e.g., exemplary universal socket 11b) comprises any combination of (1) first circular slot component 241 at a slot end 242 opposite first socket open end 25; (2)(i) horizontal slot component 244 within upper socket region 264, and (ii) a vertical slot component 245 extending from horizontal slot component 244 towards lower socket region 265; and (3) second circular slot component 247 at an intersection between horizontal slot component 244 and vertical slot component 245.

As shown in FIG. 4B, horizontal slot component 244 forms a socket flap portion 248 above horizontal slot component 244, with socket flap portion 248 having (i) a first flap end 249 connecting socket flap portion 248 to a remaining portion of universal socket 11b within upper socket region 264 and (ii) a second flap end 246 forming a portion of a periphery 251 of first socket open end 25.

As further shown in FIG. 4B, a strap connecting member 197 may be positioned above horizontal slot component 244 and along socket flap portion 248. Strap connecting member 197 may be used to connect a strap, such as exemplary strap 191, to universal socket 11b. As further shown in FIG. 4B, in desired embodiments, universal socket 11b comprises two slots 24 along opposite sides of universal socket 11b, wherein each slot comprises any combination of: (1) first circular slot component 241 at a slot end 242 opposite first socket open end 25; (2)(i) horizontal slot component 244 within upper socket region 264, and (ii) a vertical slot component 245 extending from horizontal slot component 244 towards lower socket region 265; and/or (3) second circular slot component 247 at an intersection between horizontal slot component 244 and vertical slot component 245.

Although not described herein, it should be understood that any of the components and/or features used in combination with the universal sockets disclosed in International Patent Application No. PCT/US2010/026435, the subject matter of which is incorporated herein by reference in its entirety, may also be used in combination with the artificial foot and/or artificial knee components described herein. Components and features used in combination with the universal sockets as disclosed in International Patent Application No. PCT/US2010/026435 include, but are not limited to, one or more stump cushions (e.g., exemplary stump cushions 30, 31, 32, 230 and 231; and exemplary single stump cushions 37 and 237; see FIGS. 1B, 1D and 2B-2C of International Patent Application No. PCT/US2010/026435); one or more ring sections (exemplary ring sections 40, 41 and 42; and exemplary single ring section 431; see FIGS. 1C and 1E-1G of International Patent Application No. PCT/US2010/026435); and one or more rim features (e.g., a front rim section that is at a higher position relative to a rear rim section, and/or an outer rim section that is at a higher position relative to an inner rim section; see FIGS. 5A-5B of International Patent Application No. PCT/US2010/026435).

D. A Rigid Member

As shown in FIGS. 1A-1B and 4A-4B, exemplary prosthetic devices 10, 100, 200 and 300 may further comprise a rigid member such as exemplary rigid member 12. Exemplary rigid member 12 is operatively adapted to (i) change in length so that a distance between second socket end 27 and artificial foot 13 is adjustable, and (ii) lock into a position so as to provide a fixed distance between second socket end 27 and artificial foot 13.

In some embodiments, exemplary rigid member 12 comprises (i) an upper rigid member 121 operatively adapted to attach to second socket end 27, and (ii) a lower rigid member 122 operatively adapted to attached to upper rigid member 121. Upper rigid member 121 comprises a tubular member 123 having a first cross-sectional configuration. Lower rigid member 122 comprises a solid or tubular member 124 having a second cross-sectional configuration. Lower rigid member 122 is sized so as to be insertable into an inner portion of upper rigid member 121.

Typically, upper rigid member 121 further comprises at least one row of holes 327 extending along at least a lower outer perimeter 329 of and encircling upper rigid member 121 with each hole 327 extending from an outer surface 328 into an interior volume 364 (see, FIG. 16B) of upper rigid member 121, and a plurality of first fasteners (e.g., fasteners such as exemplary fastener 270 shown in FIG. 14) operatively adapted to extend through holes 327 so as to contact and/or extend through an outer surface 331 of lower rigid member 122 and secure lower rigid member 122 within the interior volume of upper rigid member 121. In one desired embodiment, each of upper rigid member 121 and lower rigid member 122 has a circular cross-sectional configuration.

Upper rigid member 121 also comprises holes (not shown) positioned within at least one side wall 328 (see FIG. 1A) of upper rigid member 121 so as to connect upper rigid member 121 to a socket, such as exemplary universal socket 11 (i.e., 11a and 11b), via, for example, second fasteners (e.g., screws) 720, and a socket connector plate 240 as described below with reference to FIGS. 13A-13B. Lower rigid member 122 of rigid member 12 comprises rows of holes (not shown) positioned within at least one side wall to accommodate first fasteners (e.g., screws) (e.g., fasteners 270) for contacting and securing lower rigid member 122 within tubular member 340.

As discussed above, desirably, rigid member 12 is operatively adapted to (i) change in length so that a distance between second socket end 27 and artificial foot member 13 (i.e., 13a and 13b) is adjustable, and (ii) lock into a position so as to provide a fixed distance between second socket end 27 and artificial foot member 13 (i.e., 13a and 13b). Any length adjustment/locking mechanism 14 may be used to accomplish these features. For example, in one exemplary embodiment, rigid member 12 comprises two tubular members 121 and 122 (e.g., aluminum tubular members), wherein upper tubular member 121 has a larger inner diameter to allow lower tubular member 122 to slide within upper tubular member 121. Once lower tubular member 122 is positioned in a desired location within upper tubular member 121, length adjustment/locking mechanism 14 may be used to securely fix a position of lower tubular member 122 relative to upper tubular member 121.

Suitable length adjustment/locking mechanisms 14 include, but are not limited to, a clamp positioned over portions of lower tubular member 122 and upper tubular member 121; a coupling capable of attaching to an outer surface (e.g., threads along the outer surface) of each of lower tubular member 122 and upper tubular member 121; male/female coupling members positioned along lower tubular member 122 and upper tubular member 121 (e.g., grooves within upper tubular member 121 and an engaging member for engaging with one or more grooves along lower tubular member 122; and fastening members (e.g., screws) extending from an outer upper tubular member 121 toward and/or in lower tubular member 122 for securing lower tubular member 122 in a position relative to upper tubular member 121.

As discussed above and as shown in FIGS. 4A-5B, in some embodiments, rigid member 12 comprises above-knee portion 125 and below-knee portion 126. As shown in FIGS. 4A and 4B, above-knee portion 125 is represented by an upper portion of upper tubular member 121, while below-knee portion 126 is represented by a lower portion of upper tubular member 121 and lower tubular member 122.

As shown in FIGS. 11A and 11B, when rigid member 12 comprises above-knee portion 125 and below-knee portion 126, above-knee portion 125 desirably has an end configuration that enables end portion 269 of above-knee portion 125 to move within channel 184 as discussed above. Above-knee portion 125 has a flat end portion 226 and an angled cut-out end portion 227 so as to enable above-knee portion 125 of rigid member 12 to move from (1) a substantially upward direction $P_1$ (as shown in FIGS. 4A and 4B) wherein end 226 of above-knee portion 125 of rigid member 12 sits flush along channel surface 187 of forward channel rectangular cross-sectional configuration to (2) a substantially horizontal direction $P_2$ (as shown in FIGS. 4A and 4B) or (3) a downwardly extending direction $P_3$ (as shown in FIGS. 4A and 4B) wherein outer surface 225 along rear portion 269 of above-knee portion 125 of rigid member 12 is in contact with channel surface 187 of rear channel cross-sectional configuration.

Although not shown in the figures, it should be understood that rigid member 12 may comprise a length adjustment/locking mechanism 14 within above-knee portion 125 and below-knee portion 126. In this exemplary embodiment, above-knee portion 125 of rigid member 12 comprises a first upper rigid member and a first lower rigid member with a first length adjustment/locking mechanism 14 positioned therebetween, and below-knee portion 126 comprises a second upper rigid member and a second lower rigid member with a second length adjustment/locking mechanism 14 positioned therebetween so that a length of each of above-knee and below-knee portions 125 and 126 is independently adjustable.

E. Foot and Socket Connector Members

As shown in FIGS. 1A-1B and 4A-4B, exemplary prosthetic devices 10, 100, 200 and 300 may further comprise a foot or socket connector member such as exemplary foot connector member 16 and exemplary socket connector member 15.

In some exemplary embodiments, the prosthetic device of the present invention further comprises a foot connector member such as exemplary foot connector member 16, wherein exemplary foot connector member 16 comprises (i) a washer-configuration 230 having an upper surface 231, a lower surface 232, and an outer peripheral surface 233; (ii) a centrally located aperture 236 extending from lower surface 232 to upper surface 231 of exemplary foot connector member 16, the centrally located aperture 236 having an aperture cross-sectional area 237 corresponding to (a) an outer cross-sectional area of a connecting portion of rigid member 12 (e.g., lower tubular member 122 shown in FIGS. 1A-1B and 4A-4B) or (b) an outer cross-sectional area of a tubular connector 340 (discussed below) suitable for engaging with rigid member 12 (e.g., lower tubular member 122 shown in FIGS. 1A-1B and 4A-4B); (iii) a set of vertically extending holes 235 extending from lower surface 232 to upper surface 231 of exemplary foot connector member 16, each hole 235 of which is sized to accommodate a fastener (see, for example, fastener 270 shown in FIG. 14) within a set of fasteners; and (iii) a set of horizontally extending holes 234 extending from outer peripheral surface 233 to centrally located aperture 236, each hole 234 of which is sized to accommodate a fastener (see, for example, fastener 270 shown in FIG. 14) within a set of fasteners.

In some exemplary embodiments, the exemplary foot connector member 16 is used in combination with a tubular connector, such as tubular connector 340, suitable for engaging with rigid member 12 (e.g., lower tubular member 122 shown in FIGS. 1A-1B and 4A-4B). Exemplary tubular connector 340 comprises at least one row of holes 341 extending along at least an outer perimeter 342 of and encircling tubular connector 340 with each hole 341 extending from an outer surface 343 into an interior volume 346 (see, FIG. 15B) of tubular connector 340. A plurality of fasteners (see, for example, fastener 270 shown in FIG. 14) operatively adapted to extend through holes 341 may be used so as to contact and/or extend through an outer surface 124 of rigid member 12 (e.g., lower tubular member 122 shown in FIGS. 1A-1B and 4A-4B) and secure rigid member 12 (e.g., lower tubular member 122 shown in FIGS. 1A-1B and 4A-4B) within tubular connector 340.

FIG. 15A depicts a side view of exemplary tubular connector 340. As shown in FIG. 15A, exemplary tubular connector 340 further comprises foot connector end 344, rigid member connector end 345 opposite foot connector end 344, and a row of holes 347 positioned proximate foot connector end 344. Each of holes 347 extends from outer surface 343 into interior volume 346 of tubular connector 340, and is sized to accept a fastener (see, for example, fastener 270 shown in FIG. 14) extending through holes 234 of exemplary foot connector member 16.

FIG. 15B depicts a top view of exemplary tubular connector 340 showing interior volume 346 and inner surface 348. Desirably, interior volume 346 has a cross-sectional configuration that enables intimate contact with an outer cross-sectional area of a connecting portion of rigid member 12 (e.g., lower tubular member 122 shown in FIGS. 1A-1B and 4A-4B) (i.e., interior volume 346 has a slightly larger cross-sectional area and an identical cross-sectional configuration (e.g., circular) compared to the outer cross-sectional area of lower tubular member 122).

As shown in FIGS. 1A-1B and 4A-4B, exemplary foot connector member 16 attaches to an upper portion 336 of foot member outer surface 136 positioned between curved heel section 134 and second end curved section 135 of thermoformed foot member 131. Fastener (see, for example, fastener 270 shown in FIG. 14) may be used to extend through holes 235 of exemplary foot connector member 16 and through thermoformed foot member 131 along upper portion 336 (i.e., through holes 3360 along upper portion 336).

In some exemplary embodiments, the prosthetic device of the present invention further comprises a socket connector member such as exemplary socket connector member 15, wherein exemplary socket connector member 15 comprises (i) a washer-configuration 230 having an upper surface 231, a lower surface 232, and an outer peripheral surface 233; (ii) a centrally located aperture 236 extending from lower surface 232 to upper surface 231 of exemplary socket connector member 15, the centrally located aperture 236 having an aperture cross-sectional area 237 corresponding to an outer cross-sectional area of a connecting portion of rigid member 12 (e.g., upper tubular member 121 shown in FIGS. 1A-1B and 4A-4B); (iii) a set of vertically extending holes 235 extending from lower surface 232 to upper surface 231 of exemplary socket connector member 15, each hole 235 of which is sized to accommodate a fastener (see, for example, fastener 270 shown in FIG. 14) within a set of fasteners; and (iii) a set of horizontally extending holes 234 extending from outer peripheral surface 233 to centrally located aperture 236, each hole 234 of which is sized to accommodate a fastener (see, for example, fastener 270 shown in FIG. 14) within a set of fasteners.

As shown in FIGS. 1A-1B and 4A-4B, exemplary socket connector member 15 attaches to an upper end 361 of upper rigid member 121 via one or more fasteners and holes 363 within upper rigid member 121. Fastener (see, for example, fastener 270 shown in FIG. 14) may be used to extend through holes 235 of exemplary socket connector member 15 and to and/or through holes 363 positioned along upper end 361 of upper rigid member 121. As discussed below, holes 235 within exemplary socket connector member 15 may be used to connect exemplary socket connector member 15 to socket 11 (i.e., 11a and 11b) via a socket connector plate positioned within socket 11 (i.e., 11a and 11b) at second end 27.

F. A Socket Connector Plate

As discussed above, a socket connector plate, such as exemplary socket connector plate shown in FIGS. 13A-13B, may be positioned within socket 11 (i.e., 11a and 11b) at second end 27. Exemplary socket connector plate 240 comprises an upper surface 241, a lower surface 242, and an outer peripheral surface 243; and (ii) a set of vertically extending holes 245 extending from lower surface 242 to upper surface 241 of socket connector plate 240. Each hole 245 is sized to accommodate a fastener (see, for example, fastener 270 shown in FIG. 14) within a set of fasteners.

Fastener (see, for example, fastener 270 shown in FIG. 14) may be used to extend through holes 245 of exemplary socket connector plate 240 and through holes 235 within exemplary socket connector member 15.

Exemplary socket connector plate 240 is sized for placement within a lower region of universal socket 11 (i.e., 11a and 11b) proximate second socket end 27. Exemplary socket connector plate 240 in combination with socket connector member 15, and two sets of fasteners (see, for example, fastener 270 shown in FIG. 14) may be used to connect upper rigid member 121 to second socket end 27 of universal socket 11 (i.e., 11a and 11b) as shown in FIGS. 1A-1B and 4A-4B.

II. Method of Making Prosthetic Devices

The present invention further provides methods for making any of the above-described and herein described prosthetic devices and prosthetic device components. Methods for making any of the above-described prosthetic devices and prosthetic device components may comprise one or more of the following method steps:

(1) thermoforming (e.g., molding) one or more of the components (e.g., the universal socket, the rigid members, the foot, cushions, sections of the rigid member, the thermoformed foot member, etc.);

(2) cutting one or more slots (e.g., slot 24 (i.e., 24a and 24b)) and/or one or more circular slot components (e.g., first circular slot component 241) into a universal socket component and/or cutting one or more rigid members so proper length;

(3) attaching various components to one another via mechanical fasteners (e.g., bolts, screws, etc.) or chemical layers (e.g., an adhesive layer);

(4) measuring the dimensions of an amputee's stump;

(5) forming kits comprising at least one universal socket, one or more stump cushions sized to match the at least one universal socket, one or more rings or ring sections sized to match the at least one universal socket, one or more upper and lower rigid members, one or more artificial knee joints, and one or more artificial feet;

(6) forming the cushioning member;

(7) forming the sole member;

(8) forming an upper foot member;

(9) forming the universal socket;

(10) forming the rigid member, wherein the rigid member comprises (i) a single rigid member, (ii) a combination of an upper rigid member and a lower rigid member, (iii) a combination of an above-knee portion of the rigid member and a below-knee portion of the rigid member, (iv) a combination of an above-knee portion of the rigid member and a below-knee portion of the rigid member, wherein the below-knee portion comprises the upper rigid member and the lower rigid member, or (v) a combination of an above-knee portion of the rigid member and a below-knee portion of the rigid member, wherein the above-knee portion comprises a first upper rigid member and a first lower rigid member and the below-knee portion comprises a second upper rigid member and a second lower rigid member so that a length of each of the above-knee and below-knee portions is independently adjustable;

(11) forming the socket connector plate;
(12) forming the socket connector member;
(13) forming the foot connector member;
(14) forming the tubular connector;
(15) forming the artificial knee member;
(16) forming the tensioning member; and
(17) attaching one or more of the above-mentioned components to one another via (i) adhesive (e.g., attaching the thermoformed foot member to the cushioning member and the sole member); (ii) fasteners (such as screws, nuts and bolts, etc.) (e.g., attaching the universal socket to the rigid member, the socket connector plate to the socket connector member, foot connector member to the thermoformed foot member and the tubular connector, and the rigid member to the artificial knee member); or (iii) clamps (e.g., attaching the tensioning member to the artificial knee member, the above-knee portion of the rigid member, or to itself).

In some embodiments, the steps of (i) forming the socket connector member and (ii) forming the foot connector member each independently comprise: cutting the washer-configuration from a tubular member; drilling the set of vertically extending holes extending from the lower surface to the upper surface of the socket connector member or the foot connector member; and drilling the set of horizontally extending holes extending from the outer peripheral surface to the centrally located aperture.

In some embodiments, the step of forming the artificial knee member may comprise one or more of the following steps: providing a artificial knee member perform; machining the artificial knee member perform so as to form the channel extending along the upper end and through the artificial knee member perform from a front portion to a rear portion of the artificial knee member perform; drilling a horizontally extending connecting hole through an upper portion of the artificial knee member perform, the horizontally extending connecting hole extending from a first portion of an outer peripheral surface of the artificial knee member perform, out of one channel side surface, through the channel, into an opposite channel side surface, and out of a second portion of the outer peripheral surface of the artificial knee member perform opposite the first portion of the outer peripheral surface of the artificial knee member perform; machining the artificial knee member perform so as to form a centrally located hollow portion extending into a lower surface along a lower end of the artificial knee member perform, the centrally located hollow portion having a hollow portion cross-sectional area corresponding to an outer cross-sectional area of a connecting portion of a below-knee portion of a rigid member; drilling a set of horizontally extending holes extending from the outer peripheral surface of the artificial knee member preform to the centrally located hollow portion, each hole of which is sized to accommodate a fastener within a set of sixth fasteners; machining the artificial knee member perform so as to form a cut-out section along a front portion of a lower end of the artificial knee member perform; drilling a tensioning member channel (or groove) extending through the artificial knee member preform from a channel floor surface to the cut-out section along the front portion of the lower end of the artificial knee member perform; and drilling a tensioning member groove extending along the artificial knee member preform from an upper end to the cut-out section along the front portion of the lower end of the artificial knee member preform.

In some embodiments, the step of forming the universal socket comprises one or more of the following steps: forming one or more slots extending from the first socket open end towards the second socket end; forming a first circular slot component at a slot end opposite the first socket open end; forming (i) a horizontal slot component within the upper socket region, and (ii) a vertical slot component extending from the horizontal slot component towards the lower socket region; forming a second circular slot component at an intersection between the horizontal slot component and the vertical slot component; and/or forming one or more strap connecting members along a flap portion above the horizontal slot component.

It should be further noted that there is no limitation on the materials used to form the components described herein. For example, any of the above-described universal sockets may be formed from any thermoformable material, desirably a relatively inexpensive material such as polyethylene or polypropylene. Any of the rigid members and/or artificial knees may be formed from metallic, polymeric or composite materials (e.g., fiber-reinforced polymeric material), although aluminum is a preferred material. Further, the artificial foot may be formed by any thermoformable material, but, in some embodiments, is desirably a material such as CREPE neoprene material.

For example, in one desired embodiment, the following materials are used to form a given prosthetic: the universal socket—polypropylene; connector plates (e.g., socket connector plate, socket connector member and foot connector member components)—aluminum 6061; rigid member components—aluminum 6061; artificial knee components—aluminum 6061; artificial foot components (e.g., thermoformed foot member—polypropylene; and cushioning member, sole member and upper foot member—CREPE neoprene (i.e., with varying hardness)); and tensioning material—silicone rubber (e.g., surgical tubing).

III. Methods of Using Prosthetic Devices

The present invention is even further directed to methods of using any one of the above-described prosthetic devices. Methods of using any of the above-described prosthetic devices may comprise one or more of the following method steps:

(1) matching a given prosthetic device to an amputee's stump;

(2) optionally inserting one or more stump cushions into a specifically matched universal socket (i.e., matched to a specific amputee);

(3) removing a release liner to expose pressure-sensitive adhesive along an outer surface of a ring section when used;

(4) optionally attaching one or more ring sections to an inner surface of a universal socket;

(5) inserting the amputee's stump into the specifically matched universal socket until a stump end rests along an upper surface of a stump cushion;

(6) tightening the specifically matched universal socket around the amputee's stump via one or more tightening devices (e.g., straps, clamps, etc.);

(7) adjusting a length of a rigid member or rigid member components; and (8) training the amputee how to walk with the specifically matched prosthetic device.

The above-described exemplary prosthetic devices may be used immediately after an amputation operation to protect against injury during both early and preparatory stages of wound healing and the rehabilitation process. The above-described exemplary prosthetic devices provide access to bandages and dressings for wound care. Because of their ability to change and adjust the socket volume, the above-described exemplary prosthetic devices can accommodate compression and swelling of the distal stump's wound area, and accepts elastic wrap bandages to reduce swelling. Because the above-described exemplary prosthetic devices significantly reduce load on the distal stump, pressure sores and ulcers are less likely to develop at the distal end of the stump. Further, the above-described exemplary prosthetic devices allow ventilation via multiple holes 18, which may be randomly and/or evenly distributed along the socket wall to enhance postoperative healing. The above-described exemplary prosthetic devices also help maintain correct alignment in three planes of motion (i.e., frontal, sagittal, and transverse planes) and shape and prepare the residual limb for a more permanent prosthesis if so desired.

The above-described exemplary prosthetic devices are easy to fit onto the amputee's stump without requiring any tools or laboratory set up.

Additional Embodiments

The present invention is even further directed to the embodiments discussed below:

Artificial Foot Embodiments

1. A prosthetic device comprising:
    an artificial foot, said artificial foot comprising:
    a thermoformed foot member having a foot member first end, a foot member second end opposite said foot member first end, at least one foot member curved section between said foot member first end and said foot member second end, a foot member outer surface extending between said foot member first end to said foot member second end, a foot member inner surface extending between said foot member first end to said foot member second end, and a foot member thickness extending between said foot member outer surface and said foot member inner surface, wherein (a) a first portion of said foot member inner surface overlaps and faces a second portion of said foot member inner surface, (b) a foot member second end surface is positioned (i) between and connecting said foot member outer surface and said foot member inner surface to one another and (ii) over and facing said foot member inner surface, and (c) said foot member thickness is substantially constant from said foot member second end surface along said at least one foot member curved section.

2. The prosthetic device of embodiment 1, wherein said at least one foot member curved section comprises (i) a curved heel section having an arc of curvature of from about 160° to about 180°, and (ii) a second end curved section having an arc of curvature of from about 75° to about 90°.

3. The prosthetic device of embodiment 1 or 2, wherein said artificial foot further comprises:
    a cushioning member positioned along said foot member inner surface, said cushioning member operatively adapted and sized to provide a contact area for said foot member second end surface when said foot member second end surface is forced into contact with said cushioning member.

4. The prosthetic device of any one of embodiments 1 to 3, wherein said artificial foot further comprises:

a sole member positioned along a lower portion of said foot member outer surface, said sole member extending a length of said artificial foot from said foot member first end to a heel end of said artificial foot.

5. The prosthetic device of embodiment 4, wherein a heel portion of said sole member is separated from said foot member outer surface.

6. The prosthetic device of embodiment 4 or 5, wherein a toe portion of said sole member is adjacent a toe portion of said cushioning member.

7. The prosthetic device of any one of embodiments 1 to 6, wherein said foot member further comprises a groove therein, said groove (i) comprising opposing groove side surfaces, (ii) extending across a width of said foot member proximate a toe portion of said foot member, and (iii) extending a depth into said foot member from said foot member inner surface toward said foot member outer surface.

8. The prosthetic device of embodiment 7, wherein said groove extends a depth into said foot member from said foot member inner surface toward said foot member outer surface.

9. The prosthetic device of embodiment 7 or 8, wherein said groove extends a depth into said foot member from said foot member inner surface toward said foot member outer surface, said depth being less than said foot member thickness on either side of said groove.

10. The prosthetic device of embodiment 7 or 8, wherein said groove extends a depth into said foot member from said foot member inner surface toward said foot member outer surface, said depth being substantially equal to said foot member thickness on either side of said groove.

11. The prosthetic device of any one of embodiments 7 to 10, wherein said cushioning member comprises (i) a cushioning member toe portion and (ii) a cushioning member arch portion positioned on opposite sides of said groove with each independently extending across a width of said foot member on opposite sides of said groove.

12. The prosthetic device of any one of embodiments 1 to 11, further comprising an upper foot member positioned over at least a portion of (i) said cushioning member, (ii) said thermoformed foot member, or (iii) both (i) and (ii).

13. The prosthetic device of embodiment 12, wherein said upper foot member is positioned over at least a portion of said thermoformed foot member.

14. The prosthetic device of embodiment 12 or 13, wherein said upper foot member is positioned over at least a portion of said cushioning member.

15. The prosthetic device of any one of embodiments 12 to 14, wherein said upper foot member is positioned over at least a portion of (i) said cushioning member and (ii) said thermoformed foot member.

16. The prosthetic device of any one of embodiments 12 to 15, wherein said upper foot member comprises (i) an upper foot member toe portion and (ii) an upper foot member arch portion positioned on opposite sides of said groove with each independently extending across a width of said foot member on opposite sides of said groove.

17. The prosthetic device of any one of embodiments 1 to 16, wherein (i) said thermoformed foot member comprises a single layer of continuous polypropylene; (ii) said cushioning member, when present, comprises a single layer of continuous CREPE neoprene; and (iii) said sole member, when present, comprises a single layer of continuous CREPE neoprene.

18. The prosthetic device of any one of embodiments 12 to 17, wherein said upper foot member comprises, when present, a single layer of continuous CREPE neoprene.

Universal Socket Embodiments

19. The prosthetic device of any one of embodiments 1 to 18, further comprising:
 a universal socket operatively adapted and sized to receive a variety of stump sizes, said universal socket comprising:
  a first socket open end sized to receive a user stump,
  a second socket end opposite the first socket end, and
  at least two differently sized socket regions positioned between the first socket open end and the second socket end, said at least two differently sized socket regions comprising an upper socket region proximate the first socket open end and a lower socket region positioned between the upper socket region and the second socket end, wherein the upper socket region has an upper region cross-sectional area, the lower socket region has an lower region cross-sectional area, and the upper region cross-sectional area is greater than the lower region cross-sectional area; and
 a rigid member extending from and connecting said second socket end to said artificial foot.

20. The prosthetic device of embodiment 19, wherein said rigid member is operatively adapted to (i) change in length so that a distance between said second socket end and said artificial foot is adjustable, and (ii) lock into a position so as to provide a fixed distance between said second socket end and said artificial foot.

21. The prosthetic device of embodiment 19 or 20, wherein said rigid member comprises (i) an upper rigid member operatively adapted to attach to said second socket end, and (ii) a lower rigid member operatively adapted to attached to said upper rigid member.

22. The prosthetic device of embodiment 21, wherein said upper rigid member comprises a tubular member having a first cross-sectional configuration, said lower rigid member comprises a solid or tubular member having a second cross-sectional configuration, said lower rigid member is sized so as to be insertable into an inner portion of said upper rigid member.

23. The prosthetic device of embodiment 21 or 22, wherein said upper rigid member further comprises at least one row of holes extending along at least a lower outer perimeter of and encircling said upper rigid member with each hole extending from an outer surface into an interior volume of said upper rigid member, and a plurality of first fasteners operatively adapted to extend through said holes so as to contact and/or extend through an outer surface of said lower rigid member and secure said lower rigid member within said upper rigid member.

24. The prosthetic device of embodiment 22 or 23, wherein said first cross-sectional configuration comprises a circular cross-sectional configuration, and said second cross-sectional configuration comprises a circular cross-sectional configuration.

25. The prosthetic device of any one of embodiments 19 to 24, wherein said prosthetic device further comprises a socket connector plate sized for placement within a lower region of said universal socket proximate said second socket end, a socket connector member, a set of second fasteners, and a set of third fasteners, said socket connector plate, said socket connector member, and said sets of second and third fasteners being operatively adapted to connect said upper rigid member to said second socket end of said universal socket.

26. The prosthetic device of embodiment 25, wherein said socket connector member comprises (i) a washer-configuration having an upper surface, a lower surface, and an outer peripheral surface; (ii) a centrally located aperture extending from said lower surface to said upper surface of said socket connector member, said centrally located aperture having an aperture cross-sectional area corresponding to an outer cross-sectional area of a connecting portion of said rigid member; (iii) a set of vertically extending holes extending from said lower surface to said upper surface of said socket connector member, each hole of which is sized to accommodate a fastener within said set of second fasteners; and (iii) a set of horizontally extending holes extending from said outer peripheral surface to said centrally located aperture, each hole of which is sized to accommodate a fastener within said set of third fasteners.

27. The prosthetic device of any one of embodiments 19 to 26, wherein said universal socket further comprises one or more openings extending through a side wall of said universal socket from an outer surface to an inner surface of said universal socket.

28. The prosthetic device of any one of embodiments 19 to 27, wherein said universal socket further comprises one or more tightening elements operatively adapted to tighten said universal socket onto a user's stump positioned within said universal socket.

29. The prosthetic device of embodiment 28, wherein said one or more tightening elements comprise one or more straps extending along an outer surface of said universal socket.

30. The prosthetic device of embodiment 29, wherein each strap has (i) a length so as to be capable of extending along an outer perimeter of said universal socket, and (ii) at least one fastening component that enables one portion of said strap to attach to another portion of said strap.

31. The prosthetic device of any one of embodiments 28 to 30, wherein (i) a first connector portion of said one or more straps extends along an outer surface of said universal socket each strap and attaches to said outer surface of said universal socket, and (ii) and a second connector portion of said one or more straps has a first strap portion having one or more male connectors positioned along a length of said first strap portion and a second strap portion opposite said first strap portion, said second strap portion comprising one or more female connectors positioned along a length of said second strap portion, said one or more female connectors being connectable to said one or more male connectors so as to surround at least a portion of a user's leg.

32. The prosthetic device of embodiment 31, wherein said second strap portion surround at least a portion of a user's leg above the user's knee.

33. The prosthetic device of any one of embodiments 19 to 32, wherein said universal socket has a tapered configuration.

34. The prosthetic device of any one of embodiments 19 to 33, wherein said universal socket has a rim extending along said first socket open end, wherein said rim comprises at least two rim sections with at least one rim section being positioned above another rim section so as to form an uneven height of said universal socket.

35. The prosthetic device of any one of embodiments 19 to 34, wherein said universal socket further comprises at least one slot extending from said first socket open end towards said second socket end.

36. The prosthetic device of embodiment 35, wherein said universal socket further comprises a first circular slot component at a slot end opposite said first socket open end.

37. The prosthetic device of embodiment 35 or 36, wherein each slot has (i) a horizontal slot component within said upper socket region, and (ii) a vertical slot component extending from said horizontal slot component towards said lower socket region.

38. The prosthetic device of embodiment 37, wherein said universal socket further comprises a second circular slot component at an intersection between said horizontal slot component and said vertical slot component.

39. The prosthetic device of embodiment 37 or 38, wherein said horizontal slot component forms a socket flap portion above said horizontal slot component, said socket flap portion having (i) a first flap end connecting said socket flap portion to a remaining portion of said universal socket within said upper socket region and (ii) a second flap end forming a portion of a periphery of said first socket open end.

40. The prosthetic device of any one of embodiments 37 to 39, further comprising a strap connecting member positioned above said horizontal slot component.

41. The prosthetic device of embodiment 40, wherein said strap connecting member is positioned along said socket flap portion.

42. The prosthetic device of any one of embodiments 35 to 41, wherein said at least one slot comprises two slots along opposite sides of said universal socket.

68. A prosthetic device comprising:
an artificial foot;
a universal socket operatively adapted and sized to receive a variety of stump sizes, said universal socket comprising:
a first socket open end sized to receive a user stump,
a second socket end opposite the first socket end,
at least two differently sized socket regions positioned between the first socket open end and the second socket end, said at least two differently sized socket regions comprising an upper socket region proximate the first socket open end and a lower socket region positioned between the upper socket region and the second socket end, wherein the upper socket region has an upper region cross-sectional area, the lower socket region has an lower region cross-sectional area, and the upper region cross-sectional area is greater than the lower region cross-sectional area; and
at least one slot extending from said first socket open end towards said second socket end, wherein each slot has (i) a horizontal slot component within said upper socket region, and (ii) a vertical slot component extending from said horizontal slot component towards said lower socket region.

69. The prosthetic device of embodiment 68, wherein said universal socket further comprises (i) a first circular slot component at a slot end opposite said first socket open end, and (ii) a second circular slot component at an intersection between said horizontal slot component and said vertical slot component.

Artificial Foot Connector Embodiments

43. The prosthetic device of any one of embodiments 1 to 42, wherein said artificial foot further comprises:
a foot connector member attached to an upper portion of said foot member outer surface positioned between a curved heel section and a second end curved section of said thermoformed foot member.

44. The prosthetic device of embodiment 43, wherein said foot connector member comprises (i) a washer-configuration having an upper surface, a lower surface, and an outer peripheral surface; (ii) a centrally located aperture extending from said lower surface to said upper surface of said foot connector member, said centrally located aperture having an aperture cross-sectional area corresponding to (a) an outer cross-sectional area of a connecting portion of said rigid member or (b) an outer cross-sectional area of a tubular connector suitable for engaging with said rigid member; (iii) a set of vertically extending holes extending from said lower surface to said upper surface of said foot connector member, each hole of which is sized to accommodate a fastener within a set of fourth fasteners; and (iii) a set of horizontally extending holes extending from said outer peripheral surface to said centrally located aperture, each hole of which is sized to accommodate a fastener within a set of fifth fasteners.

45. The prosthetic device of embodiment 44, wherein said foot connector member further comprises a tubular connector suitable for engaging with said rigid member, said tubular connector comprising at least one row of holes extending along at least an outer perimeter of and encircling said tubular connector with each hole extending from an outer surface into an interior volume of said tubular connector, and a plurality of fifth fasteners operatively adapted to extend through said holes so as to contact and/or extend through an outer surface of said rigid member and secure said rigid member within said tubular connector.

46. The prosthetic device of embodiment 44 or 45, wherein said tubular connector engages with said lower rigid member.

Artificial Knee Embodiments

47. The prosthetic device of any one of embodiments 19 to 46, wherein said rigid member further comprises an artificial knee positioned along said rigid member.

48. The prosthetic device of embodiment 47, wherein said artificial knee comprises an artificial knee member having (i) an upper end configured to be attachable to an above-knee portion of said rigid member; (ii) a lower end configured to be attachable to a below-knee portion of said rigid member; (iii) a channel extending along said upper end and through said artificial knee member from a front portion to a rear portion of said artificial knee member, said channel having a channel surface forming opposite channel side surfaces and a channel floor surface positioned between said opposite channel side surfaces; (iv) a horizontally extending connecting hole extending through an upper portion of said artificial knee member, said horizontally extending connecting hole extending from a first portion of an outer peripheral surface of said artificial knee member, out of one channel side surface, through said channel, into an opposite channel side surface, and out of a second portion of said outer peripheral surface of said artificial knee member opposite said first portion of said outer peripheral surface of said artificial knee member; (v) a centrally located hollow portion extending into a lower surface of said lower end, said centrally located hollow portion having a hollow portion cross-sectional area corresponding to an outer cross-sectional area of a connecting portion of said below-knee portion of said rigid member; and (vi) a set of horizontally extending holes extending from said outer peripheral surface of said artificial knee member to said centrally located hollow portion, each hole of which is sized to accommodate a fastener within a set of sixth fasteners.

49. The prosthetic device of embodiment 48, wherein said artificial knee member further comprises a tensioning member channel extending through said artificial knee member from said channel floor surface to a cut-out section along said front portion of said lower end.

50. The prosthetic device of embodiment 49, wherein said tensioning member channel comprises a channel tunnel extending through said artificial knee member from said channel floor surface to said cut-out section along said front portion of said lower end, said channel tunnel having a channel tunnel surface that is not exposed along an outer surface of said artificial knee member.

51. The prosthetic device of embodiment 49, wherein said tensioning member channel comprises a channel groove extending through said artificial knee member from said channel floor surface to said cut-out section along said front portion of said lower end, said channel groove having a channel groove surface that is exposed along an outer surface of said artificial knee member.

52. The prosthetic device of any one of embodiments 49 to 51, wherein said artificial knee further comprises a tensioning member positioned along said tensioning member channel and connecting said front portion of said lower end to said above-knee portion of said rigid member.

53. The prosthetic device of embodiment 52, wherein said tensioning member comprises an elastic band material.

54. The prosthetic device of any one of embodiments 47 to 53, wherein said artificial knee enables controlled bending of said rigid member at said artificial knee joint.

Methods of Making Embodiments

55. A method of making a prosthetic device as described in any one of embodiments 1 to 54, said method comprising thermoforming the thermoformed foot member.

56. The method of embodiment 55, wherein said method further comprises one or more steps selected from:
    forming the cushioning member;
    forming the sole member;
    forming the universal socket;
    forming the rigid member, wherein the rigid member comprises (i) a single rigid member, (ii) a combination of the upper rigid member and the lower rigid member, (iii) a combination of an above-knee portion of the rigid member and a below-knee portion of the rigid member, (iv) a combination of an above-knee portion of the rigid member and a below-knee portion of the rigid member, wherein the below-knee portion comprises the upper rigid member and the lower rigid member, or (v) a combination of an above-knee portion of the rigid member and a below-knee portion of the rigid member, wherein the above-knee portion comprises a first upper rigid member and a first lower rigid member and the below-knee portion comprises a second upper rigid member and a second lower rigid member so that a length of each of the above-knee and below-knee portions is independently adjustable;
    forming the socket connector plate;
    forming the socket connector member;
    forming the foot connector member;
    forming the tubular connector;
    forming the artificial knee member;
    forming the tensioning member; and
    attaching one or more of the above-mentioned components to one another via adhesive (e.g., attaching the thermoformed foot member to the cushioning member and the sole member); fasteners (such as screws, nuts and bolts, etc.) (e.g., attaching the universal socket to the rigid member, the socket connector plate to the socket connector member, foot connector member to the thermoformed foot member and the tubular connector, and the rigid member to the artificial knee member); or clamps (e.g., attaching the tensioning member to the artificial knee member, the above-knee portion of the rigid member, or to itself).

57. The method of embodiment 56, wherein said step of forming the universal socket comprises forming one or more slots extending from the first socket open end towards the second socket end.
58. The method of embodiment 57, wherein said slot forming step further comprises forming a first circular slot component at a slot end opposite said first socket open end.
59. The method of embodiment 57 or 58, wherein said slot forming step further comprises forming (i) a horizontal slot component within the upper socket region, and (ii) a vertical slot component extending from the horizontal slot component towards the lower socket region.
60. The method of embodiment 59, wherein said slot forming step further comprises forming a second circular slot component at an intersection between the horizontal slot component and the vertical slot component.
61. The method of embodiment 59 or 60, wherein said step of forming the universal socket comprises forming one or more strap connecting members along a flap portion above the horizontal slot component.
62. The method of embodiment 56, wherein said steps of (i) forming the socket connector member and (ii) forming the foot connector member each independently comprise:
cutting the washer-configuration from a tubular member;
drilling the set of vertically extending holes extending from the lower surface to the upper surface of the socket connector member or the foot connector member; and
drilling the set of horizontally extending holes extending from the outer peripheral surface to the centrally located aperture.
63. The method of any one of embodiments 56 or 62, wherein said step of forming the artificial knee member comprises:
providing a artificial knee member perform;
machining the artificial knee member perform so as to form the channel extending along the upper end and through the artificial knee member perform from a front portion to a rear portion of the artificial knee member perform;
drilling a horizontally extending connecting hole through an upper portion of the artificial knee member perform, the horizontally extending connecting hole extending from a first portion of an outer peripheral surface of the artificial knee member perform, out of one channel side surface, through the channel, into an opposite channel side surface, and out of a second portion of the outer peripheral surface of the artificial knee member perform opposite the first portion of the outer peripheral surface of the artificial knee member perform;
machining the artificial knee member perform so as to form a centrally located hollow portion extending into a lower surface along a lower end of the artificial knee member perform, the centrally located hollow portion having a hollow portion cross-sectional area corresponding to an outer cross-sectional area of a connecting portion of a below-knee portion of a rigid member;
drilling a set of horizontally extending holes extending from the outer peripheral surface of the artificial knee member preform to the centrally located hollow portion, each hole of which is sized to accommodate a fastener within a set of sixth fasteners;
machining the artificial knee member perform so as to form a cut-out section along a front portion of a lower end of the artificial knee member perform; and
forming a tensioning member channel (or groove) extending through the artificial knee member preform from a channel floor surface to the cut-out section along the front portion of the lower end of the artificial knee member preform.
64. The method of embodiment 63, wherein said tensioning member channel forming step comprises drilling a channel tunnel through the artificial knee member from the channel floor surface to the cut-out section along the front portion of the lower end, the channel tunnel having a channel tunnel surface that is not exposed along an outer surface of the artificial knee member.
65. The method of embodiment 63, wherein said tensioning member channel forming step comprises machining a channel groove through the artificial knee member from the channel floor surface to the cut-out section along the front portion of the lower end, the channel groove having a channel groove surface that is exposed along an outer surface of the artificial knee member.

Methods of Using Embodiments

66. A method of using a prosthetic device as described in any one of embodiments 1 to 54 above.
67. A method of using a prosthetic device as described in embodiment 31, wherein the prosthetic device is attached to a portion of a user's leg such that (i) a first connector portion of the one or more straps extends along an outer surface of the universal socket and attaches to the outer surface of the universal socket, and (ii) and a second connector portion of the one or more straps has a first strap portion having one or more male connectors positioned along a length of the first strap portion and a second strap portion opposite the first strap portion, the second strap portion comprising one or more female connectors positioned along a length of the second strap portion, the one or more female connectors being connectable to the one or more male connectors so as to surround the portion of the user's leg.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

Further, it should be understood that although the above-described prosthetic devices, components thereof, and methods are described as "comprising" one or more components, features or steps, the above-described prosthetic devices, components thereof, and methods may "comprise," "consists of," or "consist essentially of" the above-described components or steps of the prosthetic devices, components thereof, and methods. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a prosthetic device, component thereof, or method that "comprises" a list of elements (e.g., components) is not necessarily limited to only those elements (or components), but may include other elements (or components) not expressly listed or inherent to the prosthetic device, component thereof, or method.

As used herein, the transitional phrases "consists of" and "consisting of" exclude any element, step, or ingredient not specified. For example, "consists of" or "consisting of" used in a claim would limit the claim to the components, materials or steps specifically recited in the claim except for impurities ordinarily associated therewith (i.e., impurities within a given composition component). When the phrase "consists of" or "consisting of" appears in a clause of the body of a claim, rather than immediately following the preamble, the phrase "consists of" or "consisting of" limits only the elements (or components) set forth in that clause; other elements (or components) are not excluded from the claim as a whole.

As used herein, the transitional phrases "consists essentially of" and "consisting essentially of" are used to define a prosthetic device, component thereof, or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Further, it should be understood that the herein-described prosthetic devices, components thereof, or methods may comprise, consist essentially of, or consist of any of the herein-described components and features, as shown in the figures with or without any feature(s) not shown in the figures. In other words, in some embodiments, the prosthetic device or component thereof of the present invention does not have any additional features other than those shown in the figures, and such additional features, not shown in the figures, are specifically excluded from the prosthetic device or component thereof. In other embodiments, the prosthetic device or component thereof of the present invention does have one or more additional features that are not shown in the figures.

What is claimed is:

1. A prosthetic device comprising:
    an artificial foot, said artificial foot comprising:
        a thermoformed foot member having a foot member first end in a toe region of said artificial foot, a foot member second end opposite said foot member first end, at least one foot member curved section between said foot member first end and said foot member second end, a foot member outer surface extending between said foot member first end to said foot member second end, a foot member inner surface extending between said foot member first end to said foot member second end, and a foot member thickness extending between said foot member outer surface and said foot member inner surface, wherein (a) a first portion of said foot member inner surface overlaps and faces a second portion of said foot member inner surface so as to form a single overlapping foot member portion, (b) a foot member second end surface (i) extends between and connects said foot member outer surface and said foot member inner surface to one another at said foot member second end, (ii) is substantially perpendicular to both said foot member outer surface and said foot member inner surface at said foot member second end, (iii) has a foot member second end surface height dimension equal to said foot member thickness at said foot member second end, and (iv) is positioned over and facing said foot member inner surface, (c) said foot member thickness is substantially constant from said foot member second end surface along said at least one foot member curved section, and (d) said artificial foot has an artificial foot length extending along said thermoformed foot member from (i) said foot member first end in the toe region of said artificial foot to (ii) a portion of said foot member outer surface at a curved heel section in a heel region of said artificial foot;
        a cushioning member positioned along and extending upward from said foot member inner surface, said cushioning member operatively adapted and sized to provide a contact area for said foot member second end surface when said foot member second end surface is forced into contact with said cushioning member; and
        a sole member positioned along a lower portion of said foot member outer surface, said sole member extending a length of said artificial foot from said foot member first end to a heel end of said artificial foot.

2. The prosthetic device of claim 1, wherein said at least one foot member curved section comprises (i) a curved heel section having an arc of curvature of from about 160° to about 180°, and (ii) a second end curved section positioned between said curved heel section and said foot member second end surface, said second end curved section having an arc of curvature of from about 75° to about 90°.

3. The prosthetic device of claim 1, wherein said foot member further comprises a groove therein, said groove (i) comprising opposing groove side surfaces, (ii) extending across a width of said foot member proximate a toe portion of said foot member, and (iii) extending a depth into said foot member from said foot member inner surface toward said foot member outer surface.

4. The prosthetic device of claim 3, wherein said cushioning member comprises (i) a cushioning member toe portion and (ii) a cushioning member arch portion positioned on opposite sides of said groove with each independently extending across a width of said foot member on opposite sides of said groove.

5. The prosthetic device of claim 3, further comprising an upper foot member positioned over at least a portion of (i) said cushioning member, or (ii) said thermoformed foot member, or (iii) both (i) and (ii).

6. The prosthetic device of claim 1, wherein (i) said thermoformed foot member comprises a single layer of continuous polypropylene; (ii) said cushioning member comprises a single layer of continuous CREPE neoprene; and (iii) said sole member comprises a single layer of continuous CREPE neoprene.

7. The prosthetic device of claim 1, further comprising:
    a universal socket operatively adapted and sized to receive a variety of stump sizes, said universal socket comprising:
        a first socket open end sized to receive a user stump,
        a second socket end opposite the first socket end,
        at least two differently sized socket regions positioned between the first socket open end and the second socket end, said at least two differently sized socket regions comprising an upper socket region proximate the first socket open end and a lower socket region positioned between the upper socket region and the second socket end, wherein the upper socket region has an upper region cross-sectional area, the lower socket region has an lower region cross-sectional area, and the upper region cross-sectional area is greater than the lower region cross-sectional area, and
        at least one slot extending from said first socket open end towards said second socket end; and
    a rigid member extending from and connecting said second socket end to said artificial foot.

8. The prosthetic device of claim 7, further comprising one or more straps operatively adapted to connect said universal socket to a user's leg, wherein (i) a first connector portion of said one or more straps extends along an outer surface of said universal socket and attaches to said outer surface of said universal socket, and (ii) a second connector portion of said one or more straps has a first strap portion having one or more male connectors positioned along a length of said first strap portion and a second strap portion opposite said first strap portion, said second strap portion comprising one or more female connectors positioned along a length of said second strap portion, said one or more female connectors being connectable to said one or more male connectors so as to surround at least a portion of the user's leg.

9. The prosthetic device of claim 7, wherein each slot has (i) a horizontal slot component extending from said first socket open end to a horizontal slot component end location within said upper socket region, and (ii) a vertical slot component extending from said horizontal slot component end location towards said lower socket region, said horizontal slot component and said vertical slot component forming a single continuous slot for each slot.

10. The prosthetic device of claim 9, wherein said horizontal slot component forms a socket flap portion above said horizontal slot component, said socket flap portion having (i) a first flap end connecting said socket flap portion to a remaining portion of said universal socket within said upper socket region and (ii) a second flap end forming a portion of a periphery of said first socket open end.

11. The prosthetic device of claim 10, wherein said at least one slot comprises two slots along opposite sides of said universal socket.

12. The prosthetic device of claim 7, wherein said rigid member further comprises an artificial knee positioned along said rigid member.

13. A prosthetic device comprising:
an artificial foot;
a universal socket operatively adapted and sized to receive a variety of stump sizes, said universal socket comprising:
a first socket open end sized to receive a user stump,
a second socket end opposite the first socket end,
at least two differently sized socket regions positioned between the first socket open end and the second socket end, said at least two differently sized socket regions comprising an upper socket region proximate the first socket open end and a lower socket region positioned between the upper socket region and the second socket end, wherein the upper socket region has an upper region cross-sectional area, the lower socket region has an lower region cross-sectional area, and the upper region cross-sectional area is greater than the lower region cross-sectional area; and
at least one slot extending from said first socket open end towards said second socket end, wherein each slot has (i) a horizontal slot component extending from said first socket open end to a horizontal slot component end location within said upper socket region, and (ii) a vertical slot component extending from said horizontal slot component end location towards said lower socket region, said horizontal slot component and said vertical slot component forming a single continuous slot for each slot.

14. The prosthetic device of claim 13, wherein said universal socket further comprises (i) a first circular slot component at a slot end opposite said first socket open end, and (ii) a second circular slot component at said location between said horizontal slot component and said vertical slot component.

15. A prosthetic device comprising:
an artificial foot, said artificial foot comprising:
a thermoformed foot member having a foot member first end in a toe region of said artificial foot, a foot member second end opposite said foot member first end, at least two foot member curved sections between said foot member first end and said foot member second end, a foot member outer surface extending between said foot member first end to said foot member second end, a foot member inner surface extending between said foot member first end to said foot member second end, and a foot member thickness extending between said foot member outer surface and said foot member inner surface, wherein (a) a first portion of said foot member inner surface overlaps and faces a second portion of said foot member inner surface so as to form a single overlapping foot member portion, (b) a foot member second end surface (i) extends between and connects said foot member outer surface and said foot member inner surface to one another at said foot member second end, (c) said foot member thickness is substantially constant from said foot member second end surface along at least two foot member curved sections, (d) said at least two foot member curved sections comprise (i) a first curved heel section having an arc of curvature of from about 160° to about 180°, and (ii) a second end curved section positioned between said curved heel section and said foot member second end surface, said second end curved section having an arc of curvature of from about 75° to about 90°, and (e) said artificial foot has an artificial foot length extending along said thermoformed foot member from (i) said foot member first end in the toe region of said artificial foot to (ii) a portion of said foot member outer surface at said first curved heel section in a heel region of said artificial foot.

16. The prosthetic device of claim 15, wherein said foot member second end surface (i) is substantially perpendicular to both said foot member outer surface and said foot member inner surface at said foot member second end, (ii) has a foot member second end surface height dimension equal to said foot member thickness at said foot member second end, and (iii) is positioned over and facing said foot member inner surface.

17. The prosthetic device of claim 15, further comprising:
a universal socket operatively adapted and sized to receive a variety of stump sizes, said universal socket comprising:
a first socket open end sized to receive a user stump,
a second socket end opposite the first socket end,
at least two differently sized socket regions positioned between the first socket open end and the second socket end, said at least two differently sized socket regions comprising an upper socket region proximate the first socket open end and a lower socket region positioned between the upper socket region and the second socket end, wherein the upper socket region has an upper region cross-sectional area, the lower socket region has an lower region cross-sectional area, and the upper region cross-sectional area is greater than the lower region cross-sectional area, and
at least one slot extending from said first socket open end towards said second socket end; and
a rigid member extending from and connecting said second socket end to said artificial foot.

* * * * *